US012661257B2

(12) United States Patent
Lowe et al.

(10) Patent No.: US 12,661,257 B2
(45) Date of Patent: *Jun. 23, 2026

(54) THERMAL PERFORMANCE OPTIMIZATION IN A THERMAL THERAPY DEVICE

(71) Applicant: Avent, Inc., Alpharetta, GA (US)

(72) Inventors: Mark H. Lowe, Danville, CA (US);
Bryan D. Huff, Vacaville, CA (US)

(73) Assignee: Avent, Inc., Alpharetta, GA (US)

( * ) Notice: Subject to any disclaimer, the term of this patent is extended or adjusted under 35 U.S.C. 154(b) by 716 days.

This patent is subject to a terminal disclaimer.

(21) Appl. No.: 18/102,492

(22) Filed: Jan. 27, 2023

(65) Prior Publication Data

US 2023/0277370 A1 Sep. 7, 2023

Related U.S. Application Data

(63) Continuation of application No. 16/455,658, filed on Jun. 27, 2019, now Pat. No. 11,596,543.

(60) Provisional application No. 62/690,875, filed on Jun. 27, 2018.

(51) Int. Cl.
*A61F 7/00* (2006.01)

(52) U.S. Cl.
CPC .............. *A61F 7/0085* (2013.01); *A61F 7/00* (2013.01); *A61F 2007/0056* (2013.01); *A61F 2007/0091* (2013.01); *A61F 2007/0093* (2013.01); *A61F 2007/0096* (2013.01)

(58) Field of Classification Search
CPC ............ A61F 7/0085; A61F 2007/0056; A61F 2007/0091; A61F 2007/0093; A61F 2007/0096
See application file for complete search history.

(56) References Cited

U.S. PATENT DOCUMENTS

| | | | |
|---|---|---|---|
| 6,508,831 B1 | 1/2003 | Kushnir et al. | |
| 6,685,731 B2 | 2/2004 | Kushnir et al. | |
| 2014/0222121 A1 | 8/2014 | Spence et al. | |

(Continued)

FOREIGN PATENT DOCUMENTS

| | | | | |
|---|---|---|---|---|
| EP | 2359781 A1 | 8/2011 | | |
| NL | 2011288 C2 * | 2/2015 | .......... | A61F 7/0085 |
| WO | 00/75577 A2 | 12/2000 | | |

(Continued)

OTHER PUBLICATIONS

Extended European Search Report dated Mar. 22, 2022 from European Application No. 19826146.3, 8 pages.

(Continued)

*Primary Examiner* — Tigist S Demie

(74) *Attorney, Agent, or Firm* — Meunier Carlin & Curfman LLC

(57) ABSTRACT

A rapid contrast therapy system can provide cold, heat/hot/warm (hereafter referred to as "hot"), and/or rapid contrast therapy, which involves rapidly alternating between cold therapy and hot therapy. The system can circulate cold or hot fluid, such as water, through a hose, into a therapy wrap, and then back to the fluid reservoirs of the system. The system can utilize a vapor compression system or other chiller technology to cool the cold water reservoir, and immersion heaters can be used to heat the hot water reservoir.

20 Claims, 26 Drawing Sheets

(56)         References Cited

U.S. PATENT DOCUMENTS

2015/0335468  A1     11/2015  Nicholas et al.
2016/0022477  A1      1/2016  Schaefer et al.

FOREIGN PATENT DOCUMENTS

WO        2016/014748  A1     1/2016
WO        2018/136814  A1     7/2018

OTHER PUBLICATIONS

International Search Report and Written Opinion issued for Application No. PCT/US2019/039625, mailed Sep. 17, 2019. 8 pages.

* cited by examiner

1000

ON/OFF
BUTTON
1004

TOUCH
DISPLAY
1002

RESERVOIR
FILL COVER
1006

HANDLES
1008

HOSE HOLSTER
1016

CONNECTOR HOSE
1018

AIR VENTS
1014

FRONT COVER
1012

1010
FOUR (4) LOCKING
CASTERS

FRONT VIEW

2000

5000

5002

2 GAL / 8 LITER
MINIMUM

| ITEM # | DESCRIPTION |
|---|---|
| 9001 | COLD RESERVOIR |
| 9002 | HOT RESERVOIR |
| 9003 | TANK LEVEL FACILITATOR |
| 9004 | FILL CAP |
| 9004A | KNOB |
| 9004B | STRAINER |
| 9004C | TANK SEAL |
| 9005 | HOT RESERVOIR VENT |
| 9006 | COLD RESERVOIR VENT |
| 9007 | FILL PORT |
| 9008 | COLD WATER LEVEL |
| 9009 | HOT WATER LEVEL |
| 9010 | COLD WATER OUTLET |
| 9011 | HOT WATER OUTLET |
| 9012 | COLD WATER INLET |
| 9013 | HOT WATER INLET |
| 9014 | HEATER BAFFLE |
| 9015 | HEATER |
| 9016 | HOT RESERVOIR PRESSURE SENSOR |
| 9017 | HOT RESERVOIR LOW LEVEL SENSOR |
| 9018 | COLD RESERVOIR PRESSURE SENSOR |
| 9019 | COLD RESERVOIR LOW LEVEL SENSOR |
| 9020 | UPPER FILL LEVEL |
| 9021 | LOWER FILL LEVEL |
| 9022 | OVERFLOW CONDUIT |
| 9023 | COLD RESERVOIR OVERFLOW DRAIN |
| 9024 | HOT RESERVOIR OVERFLOW DRAIN |

FIG. 9B

| THERAPY UP TO 2 PATIENTS | TEMPERATURE LEVELS | TREATMENT TIME | COMPRESSION LEVEL* (INTERMITTENT PNEUMATIC) | OTHER FEATURES |
|---|---|---|---|---|
| HEAT | SET MINIMUM AND MAXIMUM , IN °F OR °C | SET TOTAL THERAPY TIME | LOW & NONE | — |
| COLD | SET MINIMUM AND MAXIMUM , IN °F OR °C | SET TOTAL THERAPY TIME | LOW, MEDIUM - LOW MEDIUM, HIGH & NONE | SNOOZE FEATURE, UP TO 6 CYCLES |
| RAPID CONTRAST | SET HEAT AND COLD MINIMUM AND MAXIMUM , IN °F OR °C | SET HEAT AND COLD CYCLE TIME AND TOTAL THERAPY TIME | HEAT: LOW & NONE COLD: LOW, MEDIUM - LOW, MEDIUM, HIGH & NONE | START RAPID CONTRAST THERAPY WITH EITHER HEAT OR COLD THERAPY |
| COMPRESSION-ONLY | — | SET TOTAL THERAPY TIME | LOW, MEDIUM - LOW MEDIUM, HIGH | — |

*COMPRESSION LEVELS :

NO COMPRESSION (NONE)    LOW (5-15 mmHg)    MEDIUM - LOW (5-30 mmHg)    MEDIUM (5-50 mmHg)    HIGH (5-75 mmHg)

| | |
|---|---|
| HEAT RESERVOIR TEMPERATURE RANGE | 95 - 113°F (35-45°C) |
| COLD RESERVOIR TEMPERATURE RANGE | 38 - 60°F (3.33 -15-56°C) |
| CAPACITIES | HEAT RESERVOIR: 1 GALLON (3.79 LITERS) COLD RESERVOIR: 1 GALLON (3.79 LITERS) |
| RESERVOIR TEMPERATURE: | MAXIMUM HEAT RESERVOIR TEMPERATURE: 113°F (45°C) MAXIMUM COLD RESERVOIR TEMPERATURE: 38°F (3°C) TOLERANCE:+4°F (2°C) |

FIG. 10A

| FACTORY DEFAULT SETTINGS | | | |
|---|---|---|---|
| | MINIMUM SETTING | DEFAULT SETTING | MAXIMUM SETTING |
| RESERVOIR TEMPERATURE | | | |
| HEAT | 96°F / 35°C | 105°F / 41°C | 113°F / 45°C |
| COLD | 38°F / 3°C | 40°F / 4°C | 55°F / 13°C |
| HEAT THERAPY | | | |
| COMPRESSION LEVEL | NONE | LOW | LOW |
| TREATMENT TIME | 5 MINUTES | 15 MINUTES | 30 MINUTES |
| COLD THERAPY | | | |
| COMPRESSION LEVEL | NONE | LOW | HIGH |
| TREATMENT TIME | 5 MINUTES | 15 MINUTES | 60 MINUTES |
| SNOOZE | DISABLED | DISABLED | ENABLED |
| SNOOZE DURATION | 30 MINUTES | 30 MINUTES | 60 MINUTES |
| NUMBER OF SNOOZE CYCLES | — | 6 | — |
| COMPRESSION THERAPY | | | |
| LEVEL | LOW | LOW | HIGH |
| TREATMENT TIME | 5 MINUTES | 15 MINUTES | 60 MINUTES |

FIG. 10B

USER INTERFACE ELEMENTS

A. SCREEN TITLE

B. ACCESS SYSTEM SETTINGS

C. TOGGLE TEMPERATURE SCALE BETWEEN °F AND °C

D. SELECTED PATIENT

E. AVAILABLE THERAPIES

F. SWITCH PATIENT

G. TARGET RESERVOIR TEMPERATURE

H. DECREASE OR INCREASE TARGET TEMPERATURE

I. ACTUAL RESERVOIR TEMPERATURE

⬤ PATIENT OPTIONS
⬤ TITLES/SETTINGS
⬤ RESERVOIR OPTIONS

THERAPY ICONS

THE USER INTERFACE USES ICONS TO CONTROL THE UNIT.

| ICON | NAME | ICON | NAME |
|---|---|---|---|
| | ACCESS SYSTEM SETTINGS | | TOGGLE SNOOZE ON |
| °F/°C | TOGGLE BETWEEN FAHRENHEIT(°F) AND CELSIUS(°C) | | TOGGLE SNOOZE OFF |
| 98°F | HEAT RESERVOIR LEVEL AND CURRENT RESERVOIR TEMPERATURE | | SNOOZE TOTAL NUMBER OF CYCLES |
| 43°F | COLD RESERVOIR LEVEL AND CURRENT RESERVOIR TEMPERATURE | | SNOOZE CYCLE STATUS |
| | HEAT TEMPERATURE ALREADY SET | | HEAT THERAPY |
| | COLD TEMPERATURE ALREADY SET | | ADJUST HEAT THERAPY SETTINGS |
| | INCREASE SETTING | | RAPID CONTRAST THERAPY |
| | DECREASE SETTING | | ADJUST RAPID CONTRAST THERAPY SETTINGS |
| | START THERAPY | | SET BEGINNING THERAPY |
| | CANCEL | | RAPID CONTRAST THERAPY HEAT TIME |
| | PAUSE THERAPY | | RAPID CONTRAST THERAPY COLD TIME |
| | STOP THERAPY | | RAPID CONTRAST THERAPY TOTAL TIME |
| | PATIENT 1 ADD | | COMPRESSION-ONLY |
| | PATIENT1 SELECT | | ADJUST COMPRESSION-ONLY THERAPY SETTINGS |
| | PATIENT 1 SWITCH | | NO COMPRESSION (NONE) |
| | PATIENT 2 ADD | | LOW-COMPRESSION (5-15 mm Hg) |
| | PATIENT 2 SELECT | | MEDIUM-LOW COMPRESSION (5-30 mm Hg) |
| | PATIENT 2 SWITCH | | MEDIUM COMPRESSION (5-50 mm Hg) |
| | COLD THERAPY | | HIGH COMPRESSION (5-75 mm Hg) |
| | ADJUST COLD THERAPY SETTINGS | | ALARM |
| | | | ATTENTION: CONSULT USER MANUAL |

FIG. 11E

SYSTEM SETTINGS ICONS

THE SYSTEM SETTING USER INTERFACE USES ICONS TO CONTROL THE UNIT'S DEFAULT SETTINGS.

| ICON | NAME |
|---|---|
| | ACCESS SYSTEM SETTINGS |
| | CHANGE PERSONAL IDENTIFICATION NUMBER (PIN) |
| | FACTORY RESET |
| | LANGUAGE |
| | SYSTEM INFORMATION |
| | DATA DOWNLOAD |
| | SOFTWARE UPDATE |
| | COLD THERAPY SETTINGS |
| | COLD THERAPY TIME SETTINGS |
| | COLD THERAPY COMPRESSION SETTINGS |
| | COLD RESERVOIR TEMPERATURE SETTINGS |
| | SNOOZE SETTINGS |
| | ENABLE SNOOZE |
| | DISABLE SNOOZE |
| | HEAT THERAPY SETTINGS |
| | HEAT THERAPY TIME SETTINGS |
| | HEAT THERAPY COMPRESSION SETTINGS |

| ICON | NAME |
|---|---|
| | HEAT RESERVOIR TEMPERATURE SETTINGS |
| | RAPID CONTRAST THERAPY |
| | RAPID CONTRAST TIME SETTINGS |
| | COMPRESSION - ONLY THERAPY SETTINGS |
| | COMPRESSION - ONLY THERAPY TIME SETTINGS |
| X | CANCEL |
| ✓ | CONFIRM |
| ↰ | RETURN |
| | EXIT TO SAVE SETTINGS (RESTART REQUIRED) |
| | NO COMPRESSION (5-15 mm Hg) |
| | MEDIUM-LOW COMPRESSION (5-30 mm Hg) |
| | MEDIUM COMPRESSION (5-50 mm Hg) |
| | HIGH COMPRESSION (5-50 mm Hg) |

SYSTEM STATES

- IF A THERAPY TREATMENT IS IN SESSION, THE SYSTEM AND GUI REMAIN ON 100%
- IF THE MED4 ELITE HAS NOT BEEN IN USE FOR X TIME, THE GUI DIMS
- SCREEN SAVER MODE
- AFTER ONE HOUR OF NO USE, X
- AFTER 6 HOURS OF NO USE, THE SYSTEM AUTOMATICALLY POWERS OFF

FIG. 11F

THERMAL PERFORMANCE OPTIMIZATION IN A THERMAL THERAPY DEVICE

CROSS REFERENCE TO RELATED APPLICATIONS

This application is a continuation of U.S. patent application Ser. No. 16/455,658, filed Jun. 27, 2019, which claims the benefit of and priority to U.S. Provisional Pat. App. No. 62/690,875, filed Jun. 27, 2018, both of which are incorporated herein by reference in their entireties.

INCORPORATION BY REFERENCE

All publications and patent applications mentioned in this specification are herein incorporated by reference to the same extent as if each individual publication or patent application was specifically and individually indicated to be incorporated by reference.

FIELD

The present disclosure relates generally to thermal therapy of an animate body, and more particularly to rapid contrast therapy which alternates rapidly between cold therapy and hot therapy.

BACKGROUND

It is now common to apply cold and compression to a traumatized area of a human body to facilitate healing and prevent unwanted consequences of the trauma. In fact, the acronym RICE (Rest, Ice, Compression and Elevation) is now used by many.

Typically, thermally-controlled therapy involves cold packing with ice bags or the like to provide deep core cooling of a body part. Therapy often involves conventional therapy wraps with a fluid bladder for circulating a cooled heat exchange medium. Elastic wraps are often applied over the therapy wrap to provide compression.

More recently therapy wraps including a pair of compliant bladders to contain fluids have been disclosed. The therapy wrap typically has a compliant bladder for containing a circulating heat exchange liquid alone or in combination with a compressive bladder which overlays the compliant bladder for pressing the bladder against the body part to be subjected to heat exchange. In general, the body heat exchanging component(s) of such an apparatus include a pair of layers defining a flexible fluid bladder through which a liquid is circulated. The structure embodying both the liquid bladder and compressive bladder component is often referred to as a "wrap." The liquid fed to the wrap is maintained at a desired temperature by passing the liquid through a heat exchanging medium such as an ice bath or a refrigeration unit. One such system is disclosed, for example, in U.S. Pat. No. 6,178,562 to Elkins, the disclosure of which is herein incorporated for all purposes by reference.

In some cases, heat treatment in conjunction with cryotherapy can provide benefits to the patient when provided in a rapidly alternating manner called rapid contrast therapy. Historically, this was done by alternating immersion in hot and cold water baths. However, use of hot and cold water baths is cumbersome and inconvenient to apply. Therefore, it would be desirable to provide a system and method for conveniently delivering rapid contrast therapy, cold therapy alone, heat therapy alone, and/or compression therapy.

SUMMARY

The present disclosure relates generally to thermal therapy of an animate body, and more particularly to rapid contrast therapy which alternates rapidly between cold therapy and hot therapy.

In some embodiments, a system for providing rapid contrast therapy is provided. The system includes a cold reservoir configured to hold a cold liquid; a hot reservoir configured to hold a hot liquid; a cold fill port in fluid communication with the cold reservoir; a hot fill port in fluid communication with the hot reservoir, wherein both the cold fill port and the hot fill port are housed in a receptacle that is configured to accommodate fluid overflow from the cold reservoir and the hot reservoir by allowing the cold liquid to overflow from the cold reservoir and into the hot reservoir or the hot liquid to overflow from the hot reservoir and into the cold reservoir; a chiller configured to cool the cold liquid; a first pump configured to pump the cold liquid from the cold reservoir to the chiller; a heater configured to heat the hot liquid; a second pump configured to pump the hot liquid from the hot reservoir to the heater; a user interface configured to allow a user to set one or more parameters of the rapid contrast therapy; and a controller configured to operate the chiller, the heater, the first pump, and the second pump based on the parameters selected by the user using the user interface.

In some embodiments, the system further includes a first pressure sensor located on the bottom of the cold reservoir and a second pressure sensor located on the bottom of the hot reservoir.

In some embodiments, the system further includes a first liquid level sensor in the cold reservoir and a second liquid level sensor in the hot reservoir.

In some embodiments, the system further includes an overflow conduit extending from an upper portion of the cold reservoir to an upper portion of the hot reservoir, wherein the overflow conduit provides fluid communication between the cold reservoir and the hot reservoir.

In some embodiments, the heater is disposed in the hot reservoir.

In some embodiments, the system further includes a heating element disposed in the cold reservoir.

In some embodiments, the system further includes a heater baffle disposed proximate the heater, wherein the heater baffle is configured to induce convection of the hot liquid around the heater.

In some embodiments, the system further includes temperature sensors configured to measure a temperature of the hot liquid and a temperature of the cold liquid.

In some embodiments, the system further includes a third pump configured to pump cold liquid from the cold reservoir to a therapy wrap, and a fourth pump configured to pump hot liquid from the hot reservoir to the therapy wrap.

In some embodiments, the system further includes a compressor configured to pressurize and depressurize a therapy wrap.

In some embodiments, the controller is configured to level the liquids in the hot reservoir and the cold reservoir when the system is not being used to actively treat a patient.

In some embodiments, the controller is configured to level the liquids in the hot reservoir and the cold reservoir when the first liquid level sensor or the second liquid level sensor detects a critical liquid level.

In some embodiments, the system further includes a plurality of valves configured to control the flow of liquids throughout the system.

In some embodiments, the valves are solenoid valves.

In some embodiments, a system for providing rapid contrast therapy is provided. The system includes a cold reservoir configured to hold a cold liquid; a cold therapy supply valve in fluid communication with the cold reservoir, the cold therapy supply valve directing the flow of the cold liquid to a therapy device; a hot reservoir configured to hold a hot liquid; a hot therapy supply valve in fluid communication with the hot reservoir, the hot therapy supply valve directing the flow of the hot liquid to the therapy; and a return valve directing return flow from the therapy device to at least one of the hot and cold reservoirs; and a controller directing operation of the cold and hot therapy supply valves to control the flow of the cold liquid and the hot liquid to the therapy device, the controller directing operation of the return valve to control the return liquid flowing from the therapy device to at least one of the cold and hot reservoirs.

In some embodiments, the system further includes a first liquid level sensor in the cold reservoir to measure a level of the cold liquid; a second liquid level sensor in the hot reservoir to measure a level of the hot liquid; a first temperature sensor to measure a temperature of the cold liquid; a second temperature sensor to measure a temperature of the hot liquid; and a return temperature sensor for measuring a temperature of the return flow from the therapy device.

In some embodiments, the first temperature sensor is provided in cold liquid recirculation manifold and the second temperature sensor is provided in the hot liquid recirculation manifold.

In some embodiments, the first temperature sensor is provided in the cold liquid reservoir and the second temperature sensor is provided in the hot liquid reservoir.

In some embodiments, the controller directs return flow from the therapy device to at least one of the cold and hot reservoirs after determining that the measured liquid level within each of the cold and hot reservoirs is within a target liquid level range, wherein the controller directs the return flow to either the cold reservoir or the hot reservoir depending on the temperature of the return flow such that the return flow is directed to the reservoir containing the liquid having a closest temperature with the temperature of the return flow. The target liquid level range in each of the cold and hot reservoirs is greater than a corresponding minimum liquid level and less than a corresponding maximum liquid level.

In some embodiments, the controller directs return flow from the therapy device to at least one of the cold and hot reservoirs after determining that the measured liquid level within each of the cold and hot reservoirs is within a target liquid level range, wherein the controller directs the return flow to the hot reservoir when the temperature of the return flow is greater than an average of the temperatures of cold and hot liquids.

In some embodiments, the controller directs return flow from the therapy device to at least one of the cold and hot reservoirs after determining that the measured liquid level within each of the cold and hot reservoirs is within a target liquid level range, wherein the controller directs the return flow to the hot reservoir when the temperature of the return flow is greater than an average of the temperatures of cold and hot liquids by more than a predetermined offset amount.

In some embodiments, the predetermined offset amount is 0.5° F.

In some embodiments, the controller directs return flow from the therapy device to at least one of the cold and hot reservoirs after determining that the measured liquid level within each of the cold and hot reservoirs is within a target liquid level range, wherein controller directs return flow to the hot reservoir when the temperature of the return flow is equal to or greater than the temperature of the hot liquid in the hot reservoir.

In some embodiments, the controller directs return flow from the therapy device to at least one of the cold and hot reservoirs after determining that the measured liquid level within each of the cold and hot reservoirs is within a target liquid level range, wherein controller directs the return flow to the hot reservoir when the temperature of the return flow is greater than the temperature of the cold liquid in the cold reservoir.

In some embodiments, the controller directs return flow from the therapy device to at least one of the cold and hot reservoirs after determining that the measured liquid level within each of the cold and hot reservoirs is within a target liquid level range, wherein the controller directs the return flow to the hot reservoir when the temperature of the return flow is greater than a maximum cold reservoir return temperature.

In some embodiments, the maximum cold reservoir return temperature corresponds to the temperature of the cold liquid in the cold reservoir (measured in ° F.) plus an offset amount, In some embodiments, the wherein the offset amount is 0.5° F.

In some embodiments, the system further includes one or more conduits extending between the cold reservoir and the hot reservoir, the conduit providing fluid communication therebetween; and one or more cross-tank valves for controlling flow through the conduit; wherein the controller directs operation of the one or more cross-tank valves to control flow between the cold and hot reservoirs, wherein the controller directs operation of the one or more cross-tank valves in response to the measured liquid level in each of the cold and hot reservoirs such that the liquid level in either the cold and hot reservoirs does not exceed a maximum liquid level or fall below a minimum liquid level.

In some embodiments, the one or more cross-tank valves of the conduit is biased in a closed position.

In some embodiments, the system further includes a pump for moving liquid through the conduit.

In some embodiments, the conduit is connected to a recirculation pump for moving fluid through the conduit between the cold and hot reservoirs.

In some embodiments, the minimum liquid level of the cold and hot reservoirs is 60% of a full operating liquid level of the corresponding cold and hot reservoir.

In some embodiments, the minimum liquid level of the cold and hot reservoirs is 72% of a full operating liquid level of the corresponding cold and hot reservoirs.

In some embodiments, the minimum liquid level of the cold and hot reservoirs is 3.75". In some embodiments, the full operating liquid level of the cold and hot reservoir ranges between 5-6".

In some embodiments, the minimum liquid level is 3.6". In some embodiments, the full operating liquid level of the cold and hot reservoir ranges between 5-6".

In some embodiments, the controller directs flow through the conduit from the hot reservoir to the cold reservoir when the first liquid level sensor measures a liquid level below the minimum liquid level for the cold reservoir, wherein the controller directs flow through the conduit from the cold reservoir to the hot reservoir when the second liquid level sensor measures a liquid level below the minimum liquid level for the hot reservoir.

In some embodiments, the controller directs flow through the conduit from the cold reservoir to the hot reservoir when the first liquid level sensor measures a liquid level above the maximum liquid level for the cold reservoir, wherein controller directs flow through the conduit from the hot reservoir to the cold reservoir when the second liquid level sensor measures a liquid level above the maximum liquid level for the hot reservoir.

In some embodiments, during operation at least one of the cold and hot liquids is provided to a therapy device and the return flow is received from the therapy device and directed to the cold or hot reservoirs, wherein, during operation the controller directs operation of the cross-tank valve to open fluid communication between the reservoirs for a first time period.

In some embodiments, the controller directs cycled operation of the cross-tank valve to open and close fluid communication between the reservoirs, such that during each open-close cycle the cross-tank valve is open for the first time period and closed for a second time period until the difference between the measured liquid levels in the cold and hot reservoirs is within a predetermined deviation amount.

In some embodiments, the first time period is 5 seconds and the second time period is 5 seconds.

In some embodiments, the minimum liquid level of the cold and hot reservoirs corresponds to a liquid level where the cold and hot reservoirs indicate a critically low operating condition.

In some embodiments, the predetermined deviation amount is ¼"±⅛".

In some embodiments, the system is not operating when at least one of the cold and hot liquids have not been provided to the therapy device for a predetermined off period, wherein, when the system is not operating, the controller directs operation of the cross-tank valve to open fluid communication between the reservoirs for a first time period.

In some embodiments, the predetermined off period that the therapy system is not operating is less than or equal to 20 seconds.

In some embodiments, the predetermined off period that the therapy system is not operating is at least 5 second.

In some embodiments, the predetermined off period that the therapy system is not operating is at least 10 seconds.

In some embodiments, the controller directs operation of the cross-tank valve to open fluid communication between the reservoirs until the difference between the measured liquid levels in the cold and hot reservoirs is within a predetermined deviation amount.

In some embodiments, the predetermined deviation amount is ¼"±⅛".

In some embodiments, the controller directs cycled operation of the cross-tank valve to open and close fluid communication between the reservoirs, such that during each open-close cycle the cross-tank valve is open for the first time period and closed for a second time period until the difference between the measured liquid levels in the cold and hot reservoirs is within a predetermined deviation amount.

In some embodiments, the first time period is 5 seconds and the second time period is 5 seconds.

In some embodiments, the predetermined deviation amount is ¼"±⅛".

In some embodiments, the return valve comprises a cold reservoir return valve and a hot reservoir return valve, wherein the cold reservoir return valve directs return flow from the therapy device to the cold reservoir, wherein the hot reservoir return valve directs return flow from the therapy device to the hot reservoir.

In some embodiments, the system further includes at least one of the cold therapy supply valve, the hot therapy supply valve, the return valve and the cross-tank valve can be adjusted by the controller to vary at least one of a flow rate, volume, flow pressure, and temperature of the flow of liquid therethrough.

In some embodiments, the return temperature sensor is provided upstream of the return valve such that the return temperature sensor is between an output of the therapy device and the return valve.

In some embodiments, the therapy device comprises a therapy wrap configured for wrapping to a portion of an animate body for delivering treatment.

In some embodiments, the cold reservoir includes a cold reservoir fill port and the hot reservoir includes a hot reservoir fill port, wherein the cold and hot reservoir fill ports are housed in a receptacle that is configured to accommodate fluid overflow from the cold reservoir and the hot reservoir by allowing the cold liquid to overflow from the cold reservoir and into the hot reservoir or the hot liquid to overflow from the hot reservoir and into the cold reservoir.

In some embodiments, the system further includes a first pump configured to pump cold liquid from the cold reservoir to the therapy device; and a second pump configured to pump hot liquid from the hot reservoir to the therapy device.

In some embodiments, the system further includes a chiller configured to cool the cold liquid, and a third pump (recirculating pump) configured to pump the cold liquid from the cold reservoir to the chiller.

In some embodiments, the third pump (recirculating pump) is configured to pump cold liquid to the hot reservoir.

In some embodiments, the third pump is located upstream of the first pump.

In some embodiments, the cold therapy supply valve is located downstream from the first pump In some embodiments, the system further includes a heater configured to heat the hot liquid; and a fourth pump (recirculating pump) configured to pump the hot liquid from the hot reservoir to the heater.

In some embodiments, the heater is disposed in the hot reservoir.

In some embodiments, the system further includes a heater baffle disposed proximate the heater, wherein the heater baffle is configured to induce convection of the hot liquid around the heater.

In some embodiments, the fourth pump (recirculating pump) is configured to pump hot liquid to the cold reservoir.

In some embodiments, the fourth pump is located upstream of the second pump.

In some embodiments, the hot therapy supply valve is located downstream from the second pump.

In some embodiments, the system further includes a first pressure sensor located on the bottom of the cold reservoir, and a second pressure sensor located on the bottom of the hot reservoir.

In some embodiments, the system further includes a heating element disposed in the cold reservoir.

In some embodiments, the system further includes an overflow conduit extending from an upper portion of the cold reservoir to an upper portion of the hot reservoir, wherein the overflow conduit provides fluid communication between the cold reservoir and the hot reservoir.

In some embodiments, the system further includes a compressor configured to pressurize the therapy device.

In some embodiments, the system further includes a user interface configured to allow a user to set one or more parameters of the rapid contrast therapy; and wherein the controller operates at least one of a chiller, a heater, the first pump, and the second pump based on the parameters selected by the user using the user interface.

In some embodiments, a method for providing rapid contrast therapy using a rapid contrast therapy device is provided. The method includes applying a therapy wrap to a patient; connecting a therapy wrap connector to a treatment device connector, the therapy device connector providing fluid communication between the therapy wrap and a cold therapy supply line, a hot therapy supply line and a pressurized gas supply line; measuring a liquid level of a cold and hot liquid within a cold and hot liquid reservoir provided in the therapy device; confirming a measured liquid level within each of the cold and hot reservoirs is within a target liquid level range; providing at least one of a temperature therapy and a pressure therapy to the patient via the therapy wrap by directing at least one of a cold liquid, a hot liquid and a pressurized gas through therapy wrap via a corresponding cold therapy supply valve, hot therapy supply valve and gas therapy supply valve; controlling via a return valve a return flow of the liquid from the therapy wrap to at least one of the cold and hot reservoirs to minimize the unnecessary thermal pollution of hot water from entering the cold tank or cold water from entering the hot tank upon return from the therapy wrap.

In some embodiments, the method the return flow is directed to either the cold reservoir or the hot reservoir depending on the temperature of the return flow such that the return flow is directed to the reservoir containing the liquid having a closest temperature with the temperature of the return flow.

In some embodiments, the return flow is directed to the hot reservoir when the temperature of the return flow is greater than an average of the temperatures of cold and hot liquids.

In some embodiments, the return flow is directed to the hot reservoir when the temperature of the return flow is greater than an average of the temperatures of cold and hot liquids by more than a predetermined offset amount.

In some embodiments, the predetermined offset amount is 0.5° F.

In some embodiments, the return flow is directed to the hot reservoir when the temperature of the return flow is equal to or greater than the temperature of the hot liquid in the hot reservoir.

In some embodiments, the return flow is directed to the hot reservoir when the temperature of the return flow is greater than the temperature of the cold liquid in the cold reservoir.

In some embodiments, the return flow is directed to the hot reservoir when the temperature of the return flow is greater than a maximum cold reservoir return temperature.

In some embodiments, the maximum cold reservoir return temperature corresponds to the temperature of the cold liquid in the cold reservoir (measured in ° F.) plus an offset amount, In some embodiments, the offset amount is 0.5° F.

In some embodiments, the measured liquid level within either of the cold and hot reservoirs is not within a target liquid level range the return flow is directed to either the cold reservoir or the hot reservoir depending on the measured liquid level in each of the cold and hot reservoirs such that the measured liquid level in the cold and hot reservoirs does not exceed the corresponding maximum liquid level or fall below the corresponding minimum liquid level.

In some embodiments, the return flow is directed to the cold reservoir when the first liquid level sensor measures a liquid level below the minimum liquid level for the cold reservoir, and wherein the return flow is directed to the hot reservoir when the second liquid level sensor measures a liquid level below the minimum liquid level for the hot reservoir.

In some embodiments, the return flow is directed to the hot reservoir when the first liquid level sensor measures a liquid level above a maximum liquid level for the cold reservoir, and wherein return flow is directed to the cold reservoir when the second liquid level sensor measures a liquid level above the maximum liquid level for the hot reservoir.

In some embodiments, the method further includes directing a cross-tank flow of the cold and hot liquids between the cold and hot reservoirs via a conduit operated by a cross-tank valve, where the cross-tank flow is directed in response to the measured liquid levels in each of the cold and hot reservoirs such that the liquid level in either the cold and hot reservoirs does not exceed a maximum liquid level or fall below a minimum liquid level.

In some embodiments, the method further includes directing flow through the conduit from the hot reservoir to the cold reservoir when the first liquid level sensor measures a liquid level below the minimum liquid level for the cold reservoir.

In some embodiments, the method further includes directing flow through the conduit from the cold reservoir to the hot reservoir when the second liquid level sensor measures a liquid level below the minimum liquid level for the hot reservoir.

In some embodiments, the method further includes directing flow through the conduit from the cold reservoir to the hot reservoir when the first liquid level sensor measures a liquid level above the maximum liquid level for the cold reservoir.

In some embodiments, the method further includes directing flow through the conduit from the hot reservoir to the cold reservoir when the second liquid level sensor measures a liquid level above the maximum liquid level for the hot reservoir.

In some embodiments, the during operation of the therapy device at least one of the cold and hot liquids is provided to the therapy wrap and the return flow is received from the therapy wrap and directed to the cold or hot reservoirs, wherein during operation of the therapy device, directing operation of the cross-tank valve to open fluid communication between the reservoirs for a first time period.

In some embodiments, the method further includes directing cycled operation of the cross-tank valve to open and close fluid communication between the reservoirs, such that during each open-close cycle the cross-tank valve is open for the first time period and closed for a second time period until the difference between the measured liquid levels in the cold and hot reservoirs is within a predetermined deviation amount.

In some embodiments, the minimum liquid level of the of the cold and hot reservoirs corresponds to a liquid level where the cold and hot reservoirs indicate a critically low operating condition.

In some embodiments, the therapy device is not operating when at least one of the cold and hot liquids have not been provided to the therapy wrap for a predetermined off period, when the therapy device is not operating, directing operation of the cross-tank valve to open fluid communication between the reservoirs for a first time period.

In some embodiments, the method further includes directing cycled operation of the cross-tank valve to open and close fluid communication between the reservoirs, such that during each open-close cycle the cross-tank valve is open for the first time period and closed for a second time period until the difference between the measured liquid levels in the cold and hot reservoirs is within a predetermined deviation amount.

BRIEF DESCRIPTION OF THE DRAWINGS

The novel features of the disclosure are set forth with particularity in the claims that follow. A better understanding of the features and advantages of the present disclosure will be obtained by reference to the following detailed description that sets forth illustrative embodiments, in which the principles of the disclosure are utilized, and the accompanying drawings of which:

FIGS. 9A and 9B illustrate an embodiment of a cold reservoir and a hot reservoir.

FIG. 10A-10B present various parameters that are used by the system.

DETAILED DESCRIPTION

Figure 1A:
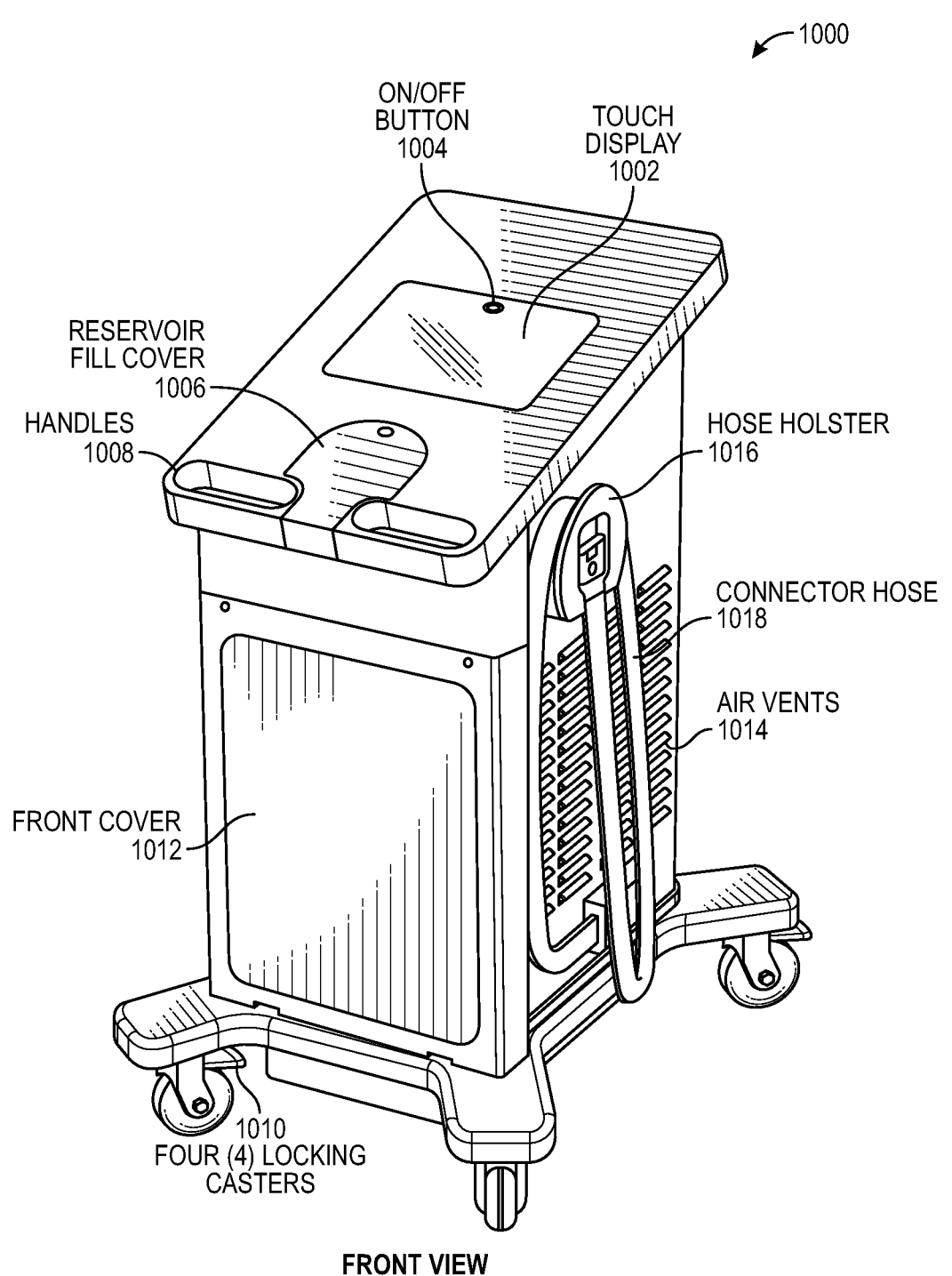
FIGS. 1A-1B illustrate a system for providing cold, heat/hot/warm (hereafter referred to as "hot"), and/or rapid contrast therapy.
Figure 1B:
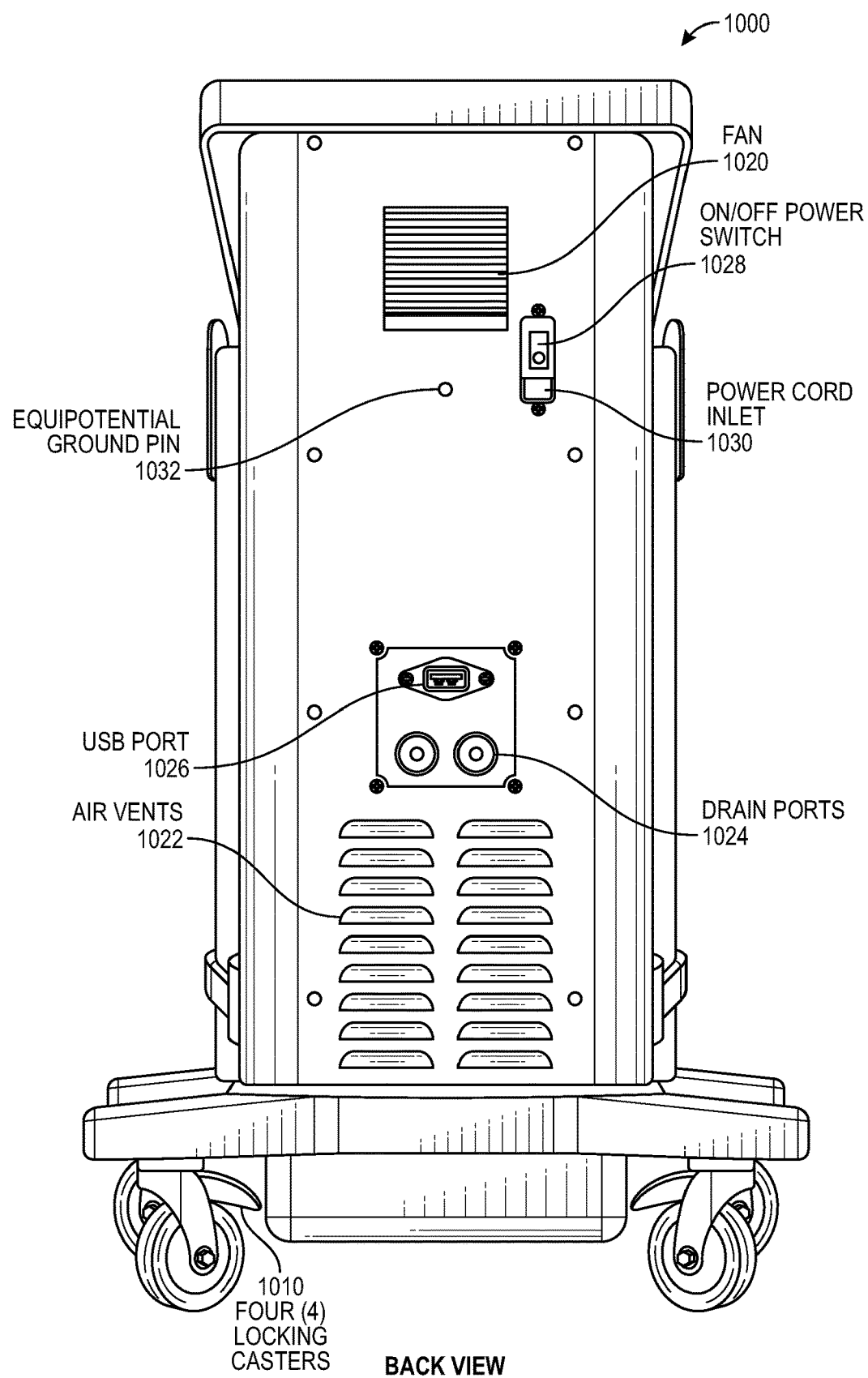

FIGS. 1A-1B and illustrate a system 1000 for providing cold, heat/hot/warm (hereafter referred to as "hot"), and/or rapid contrast therapy, which involves rapidly alternating between cold therapy and hot therapy. The system can circulate cold or warm fluid, such as water, through a hose, into a therapy wrap, and then back to the fluid reservoirs of the system. The system can utilize a vapor compression system or other chiller technology to cool the cold water reservoir, and immersion heaters can be used to heat the hot water reservoir. The system can have two or more ports, in order to serve two or more patients simultaneously. Two or more air pumps can be utilized (one for each port) in order to provide pneumatic compression along with the thermal therapy. In other embodiments, the system may have a single port and single air pump to treat just a single patient.

In some embodiments, the system 1000 can have a user interface 1002 on an upper front facing panel. The user interface 1002 can be a touch display. An on/off power button 1004 can be provided. The on/off power button can be located on, in or near the user interface 1002. The upper front facing panel can also have a reservoir fill cover 1006 that can be opened to provide access to fill ports. Handles 1008 can also be provided to allow the user to move the system, which can have a base with 4 locking casters 1010. A removable or openable front cover 1012 can provide access to the internal components of the system. Air vents 1014, a hose holster 1016, and a connector hose 1018 can be located on one or both the sides of the system.

The rear of the system can have a fan 1020, additional air vents 1022, drain ports 1024, a USB port 1026 and/or network port, an additional on/off power switch 1028, a power cord inlet 1030, and equipotential ground pins 1032.

Therapy Modalities:

COOLING: water can be supplied and returned to the cold reservoir as controlled by the flow control valves associated with the port. Since there is only one cold reservoir in some embodiments, the cold reservoir temperature control may be common to both ports, or all ports for embodiments with more than 2 ports, and the temperature may be adjustable from the user interface, such as the home screen which can be the default display screen. Each port can have individual settings for treatment parameters, including treatment temperatures and duration and air pressure, which allow the system to deliver customized treatment to each wrap connected to the system.

HEATING: water can be supplied and returned to the hot reservoir as controlled by the flow control valves associated with the port. Since there may be only one hot reservoir in some embodiments, the hot reservoir temperature control may be common to both ports, or all ports for embodiments with more than 2 ports, and its temperature may be adjustable from the user interface, such as the home screen which can be the default display screen. Each port can have individual settings for treatment parameters, including treatment temperatures and duration and air pressure, which allow the system to deliver customized treatment to each wrap connected to the system.

CONTRAST: water supplied to the wraps can alternate between the hot and cold reservoirs based on the separate and customizable hot duration and temperature and cold duration and temperature settings. A typical treatment is alternating 3 min hot and 1 min cold. In some embodiments, durations of less than one min on either hot or cold therapy to prevent the wraps from being half filled with warm/hot water and half filled with cold water. Air pressure can also be adjustable separately for the hot and cold treatments. For example the pressure could be set to high (i.e., 75 mmHg) during cold and med low (i.e., 25 mmHg) during hot. In some embodiments, the pressure applied during cold treatment can be higher during cold treatment than hot treatment to work alongside with vasoconstriction during cold treatment. Heat causes vasodilation, and blood rushes in—so air pressure may be counterproductive with heat therapy, which means using a lower pressure during heat treatment may be beneficial. In some embodiments, treatment duration selections may be limited to whole cycle values to end in a certain mode. For example, a hot and cold cycle may be limited to minute increments, and a combined hot and cold cycle duration may be limited to a set value or upper limit. For example, the single combined hot cold cycle may not exceed 4 minutes in some embodiments, meaning if the hot treatment is 3 minutes, then the cold treatment is 1 minute. In some embodiments, a hot cold cycle may be limited to 2 to 10 minutes, or 4 to 20 minutes, or 2 to 30 minutes. In some embodiments, the total treatment is configured to end with cold treatment or hot treatment by configuring the treatment times and number of cycles.

COMPRESSION ONLY: water is not pumped through the wraps but air or another gas can be pumped into the wrap. Treatment duration, air pressure, and optionally the pressure curve profile (the ramping up, maintenance, and release of pressure over time) will be adjustable.

COMPRESSION WITH THERMAL THERAPY: The thermal therapies described herein can be combined with the compression therapy.

Figure 2:
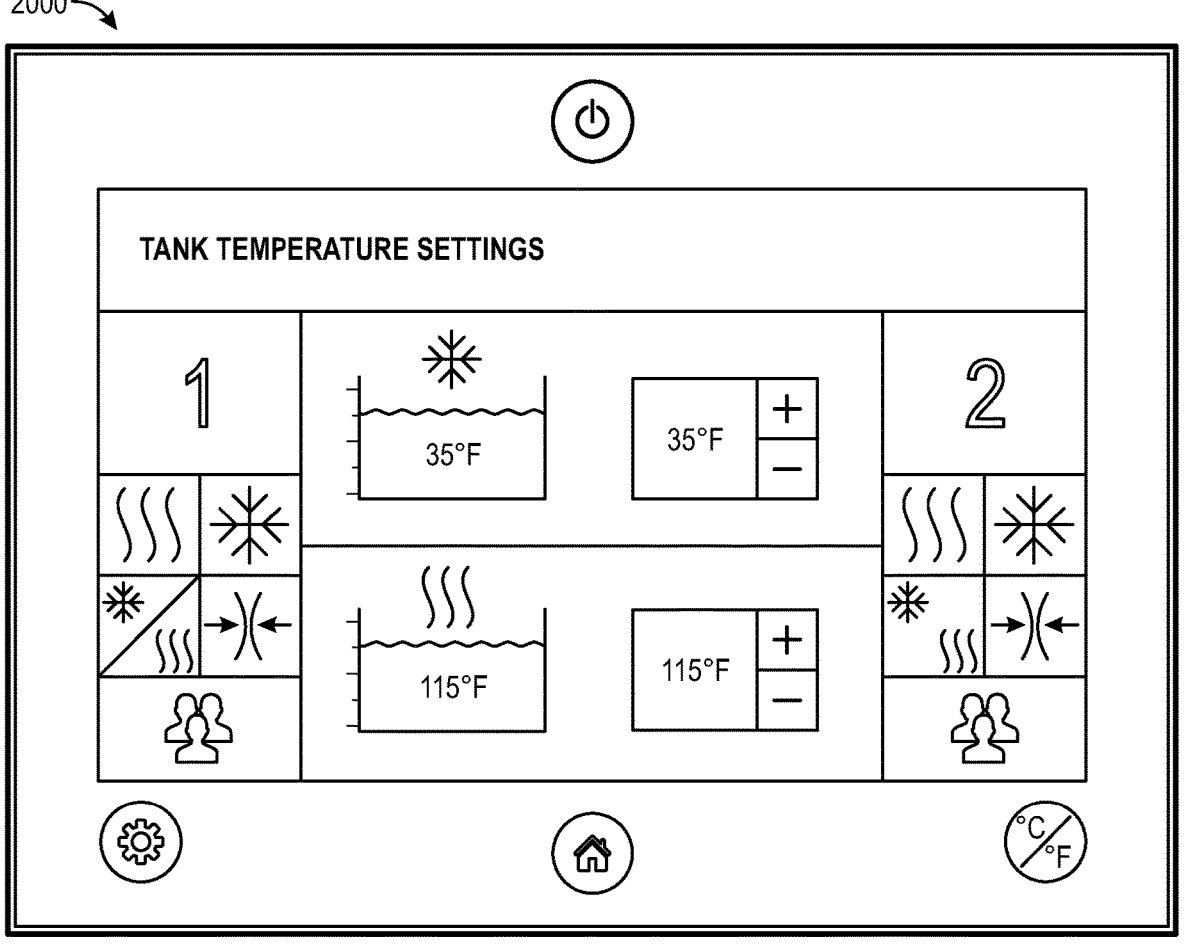
FIG. 2 illustrates an embodiment of a user interface that can serve as a control panel.

Control Panel(S):

FIG. 2 illustrates an embodiment of a user interface 2000 that can serve as a control panel. The user interface 2000 can be a touch screen with graphical icons that represent the different treatment modalities and can include adjustable parameter settings, such as hot and cold temperature settings for example. For example, the control panel can use a 7" touchscreen TFT set in a traditional domed membrane switch. Most of the controls can be on the TFT display. A few buttons like power, STOP, home, etc. can be on the membrane switch. In some embodiments, a capacitive touch screen can be used.

Air Pressure Profiles:

In various embodiments, in the cooling mode the pressure of gas furnished by the control unit is between about 0.25 psig and about 20 psig, preferably between about 0.25 psig and about 5 psig, and more preferably about 0.25 to about 1.5 psig. In various embodiments, the control unit maintains a compressive force of between about 0.25 psig and about 5 psig. In various embodiments, the control unit maintains a compressive force of between about 0.25 psig and about 0.5 psig. In various embodiments, the pressure of gas furnished by the control unit is user selectable in increments of 5 mm Hg from 0 mm to about 75 mm.

In various embodiments, the pressure of gas furnished by the control unit is based on the patient's response. For example, if the patient is wearing the wrap during exercise, the pressure may vary based on how strenuous the exercise is. If the patient is having trouble breathing, the control unit may decrease the compressive force around the lungs. The pressure profile map may be set to adjust based on a predetermined routine. In various embodiments, the pressure profile map includes 3 minutes of slowly increasing pressure followed by 2 minutes of decreasing pressure. In various embodiments, the pressure profile map includes 30 seconds of increasing pressure followed by 15 seconds of decreasing pressure. In various embodiments, the pressure fluctuates at random. In various embodiments, the pressure profile map includes 2 minutes of compression followed by 1 minute with no compression.

The strength and frequency of the pulses may be modified depending on the application. In various embodiments, the control unit delivers pulses of compression for massaging therapy.

In various embodiments the wrap can be used with a rigid or semi-rigid support such as a brace. In various embodiments, the control unit can apply and maintain a low pressure or no pressure when the control unit detects a brace in use with the wrap. In various embodiments, the control unit can apply and maintain higher pressures when the control unit detects a brace not in use with the wrap. In some embodiments, a low pressure is less than 10 psig, 5 psig, 4 psig, 3 psig, 2 psig, 1 psig, or 0.5 psig. In some embodiments, a high pressure is greater than 0.5 psig, 1 psig, 2 psig, 3 psig, 4 psig, 5 psig, or 10 psig.

In heating mode, the same pressures will be available as for the cold settings.

Figure 3:
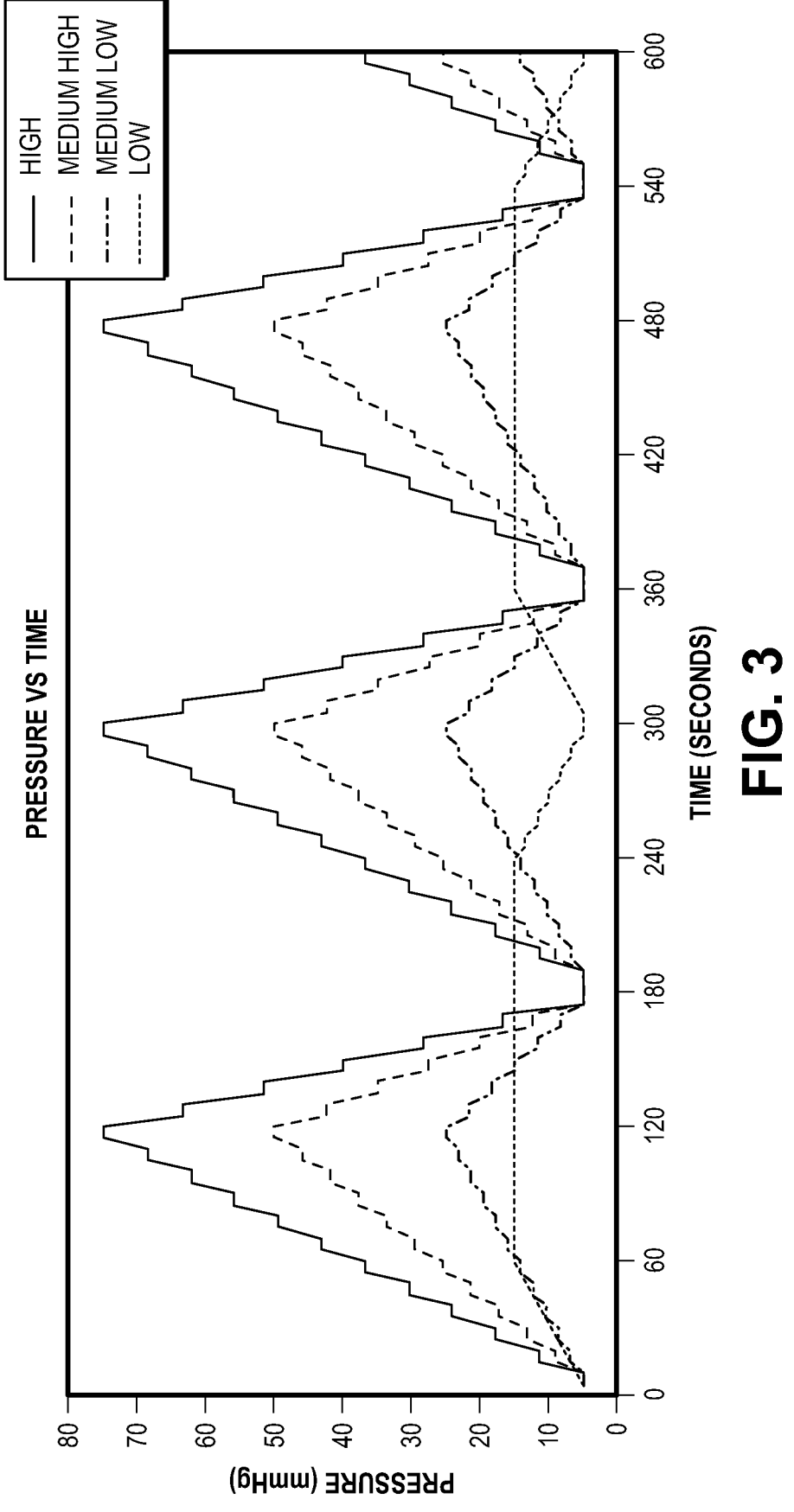
FIG. 3 illustrates various pressure curve profiles.

FIG. 3 illustrates various pressure curve profiles: high (about 75 mmHg), medium high (about 50 mmHg), medium low (about 25 mmHg), and low (about 15 mmHg). The ramp time can be about 2 minutes to achieve the target pressure for high, medium high, and medium low, while the ramp time for low can be about 1 minute. The ramp times and target temperatures for the different settings can be adjustable, or can be predetermined and fixed.

In some embodiments, the default pressures for the cooling and heating modes is different. In other embodiments, the default pressures for the cooling and heating modes is the same.

In contrast therapy mode, the therapy profile can specify the cold duration and temperature and compression, the hot duration and temperature and compression, and the duration of treatment or number of cycles to be run.

In some embodiments, the system allows named preset therapy sessions to be configured and saved by the user that can be later selected directly by name and/or a unique icon.

Wraps:

Further details regarding wraps, fluid bladders, air bladders, and their operation and manufacture are described in U.S. Pat. Nos. 7,837,638; 7,198,093 and 6,695,872, both to Elkins, U.S. Patent Publication Nos. 2014/0142473, the entire contents of which are incorporated herein for all purposes by reference.

Figure 4A:
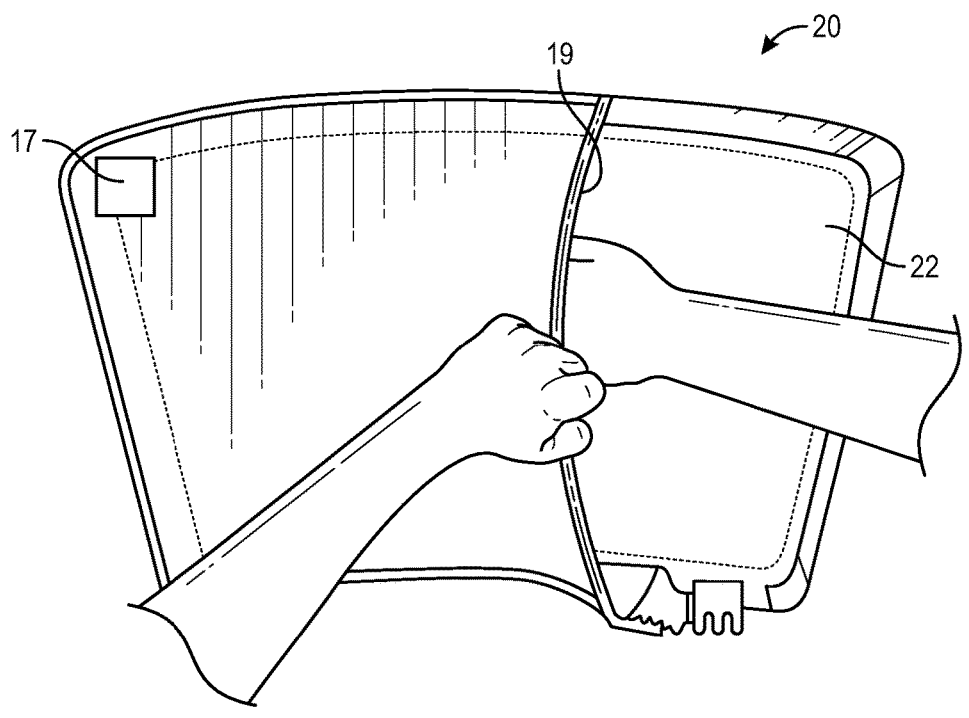
FIGS. 4A and 4B illustrate an embodiment of a therapy wrap.
Figure 4B:
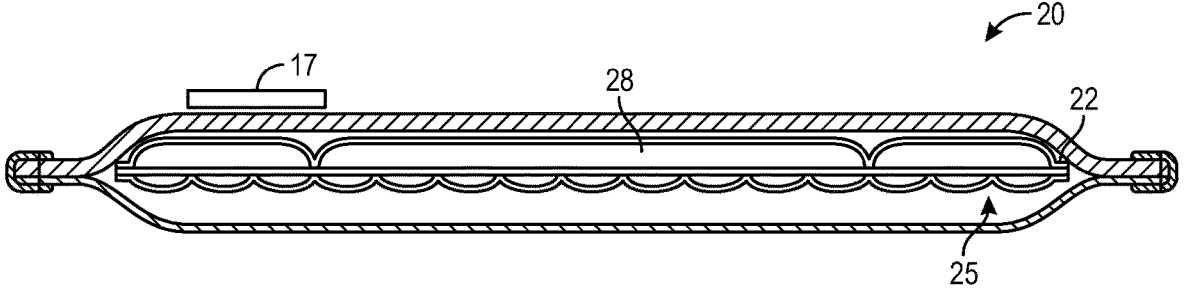

FIGS. 4A and 4B illustrate an embodiment of a therapy wrap. The therapy wrap 20 is configured for wrapping to a portion of an animate body for delivering treatment. The body may include, but is not limited to, a mammalian body such as a human or an equine animal. The exemplary therapy wrap is in the form of a sleeve for connecting various components of heat transfer device 22 to the patient's body. The sleeve is similar in many respects to the sleeve disclosed by U.S. Pat. No. 7,896,910 to Schirrmacher et al. and cover disclosed by U.S. Pat. No. 6,695,872 to Elkins, the entire contents of which patents are incorporated herein for all purposes by reference.

Exemplary therapy wrap 20 includes an opening 19 for directing heat transfer device 22 into a pouch or cavity in the sleeve interior. A portion of sleeve may be pulled back to reveal the pouch and facilitate positioning of the heat transfer device in the pouch as shown in FIG. 4A. Any suitable fastening means can be used to close the opening such as, but not limited to, a zipper.

The pouches may be selectively positioned in predetermined locations on therapy wrap 20. In other words, the pouches may be fixed into a position on the wrap based on parameters defined before use of the wrap. Such parameters may include user preferences or application demands. In various embodiments, the sleeve is configured to position a bladder in one of a plurality of predefined locations. The predefined locations may be determined by user preferences. In various embodiments, the predefined locations correspond to key areas for core cooling of the body.

Therapy wrap 20 may have a variety of shapes and sizes for applying to different portions of the body or different body anatomies. The sleeve may be shaped and configured for application to a mammal, and in various embodiments, a human. In various embodiments, the sleeve is shaped for applying to and covering all or part of a torso, a thoracic region, a cranial region, a throat region, a limb, and a combination of the same. Various aspects of the therapy wrap, in particular the sleeve, shape and design may be similar to the devices disclosed by U.S. Pat. No. 7,107,629 to Miros et al. and U.S. Patent Pub. No. 2005/0256556 A1 to Schirrmacher et al., the entire contents of which are incorporated herein for all purposes by reference.

In general, "heat transfer device" refers to the body heat exchanging component(s). In various embodiments, the heat transfer device includes layers of material defining a flexible fluid bladder through which a liquid is circulated and a gas bladder in which a pressurized gas is injected. Exemplary heat transfer device 22 is in the form of a conventional multi-bladder assembly for positioning adjacent a treatment site of a body. In various aspects, the multi-bladder assembly is manufactured and configured using known techniques. A commonly used thermal bladder assembly uses both a compliant fluid bladder 25 for circulating heat transfer fluid and a gas pressure bladder 28 which overlays the fluid bladder (best seen in FIG. 4B). The gas pressure bladder is adapted to inhibit edema and/or for pressing the fluid bladder against the body part to be subjected to heat exchange.

More specifically, outer gas pressure bladder 28 is adapted to receive a first fluid such as a gas (e.g., air) that can be regulated to provide the desired amount of inflation of the bladder or pressure therein. This inflation or pressure affects the compressive force applied to the animate body during use. Inner fluid bladder 25 is adapted to receive a fluid, such as a coolant which can be in the form of a cold liquid, to transfer heat away from the animate body part. Alternatively, the fluid supplied to the inner bladder can have a temperature higher than the animate body part to heat the body part.

The hose and connector to attach the therapy wrap to the system can use a 3-port connector with a fluid inlet, a fluid outlet, and a gas port.

Approximate Dimensions for One Embodiment of the System

| Height | 40 inches | 1016 mm |
| Length | 20 inches | 500 mm |
| Width | 17 inches | 430 mm |
| Water Volume | 3 gallon (1-5 gallons) | 11 liter |
| Weight | 150 pounds | 45 Kg |

Water Temperatures:

In some embodiments, the temperature of the hot reservoir can be adjustable from about 100 to 120 degF, and the temperature of the cold reservoir can be adjustable from about 38 to 60 degF. The temperature ranges can be determined by safety considerations (i.e., avoiding tissue damage) and freeze prevention of fluid in cold reservoir. In some embodiments, the range limits can be adjusted by the user. For example the upper range for the hot reservoir can be lowered by the user to, for example, 110 or 115 F, and/or the lower range for the cold reservoir can be increased to 40 or 45 or 50 F. In some embodiments, the user adjustable range is limited to adjustments made within a predetermined range so that the user cannot exceed a predetermined hot temperature limit or fall below a predetermined cold temperature limit.

Water:

In some embodiments, distilled water is provided and/or recommended for use to reduce scaling. In the event distilled water is not used, descaling agents such as phosphoric acid, acetic acid, or citric acid can be flushed through the system. Instructions for descaling the system can be provided.

In some embodiments, addition of an antimicrobial and or scale inhibiter may also be recommended.

Figure 5A:
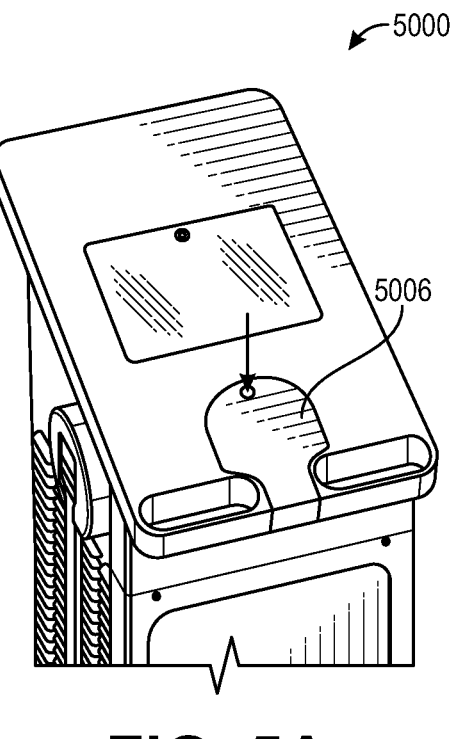
FIGS. 5A-5C illustrate an embodiment of the system being refilled using the refill port and drained using the drain ports.
Figure 5B:
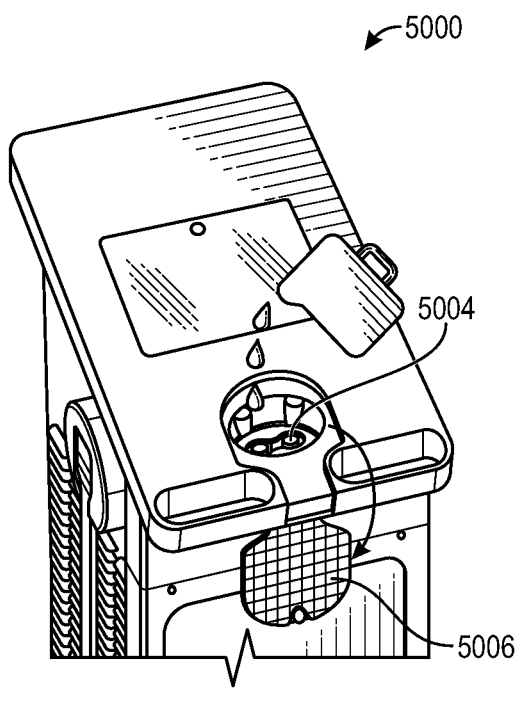
Figure 5C:
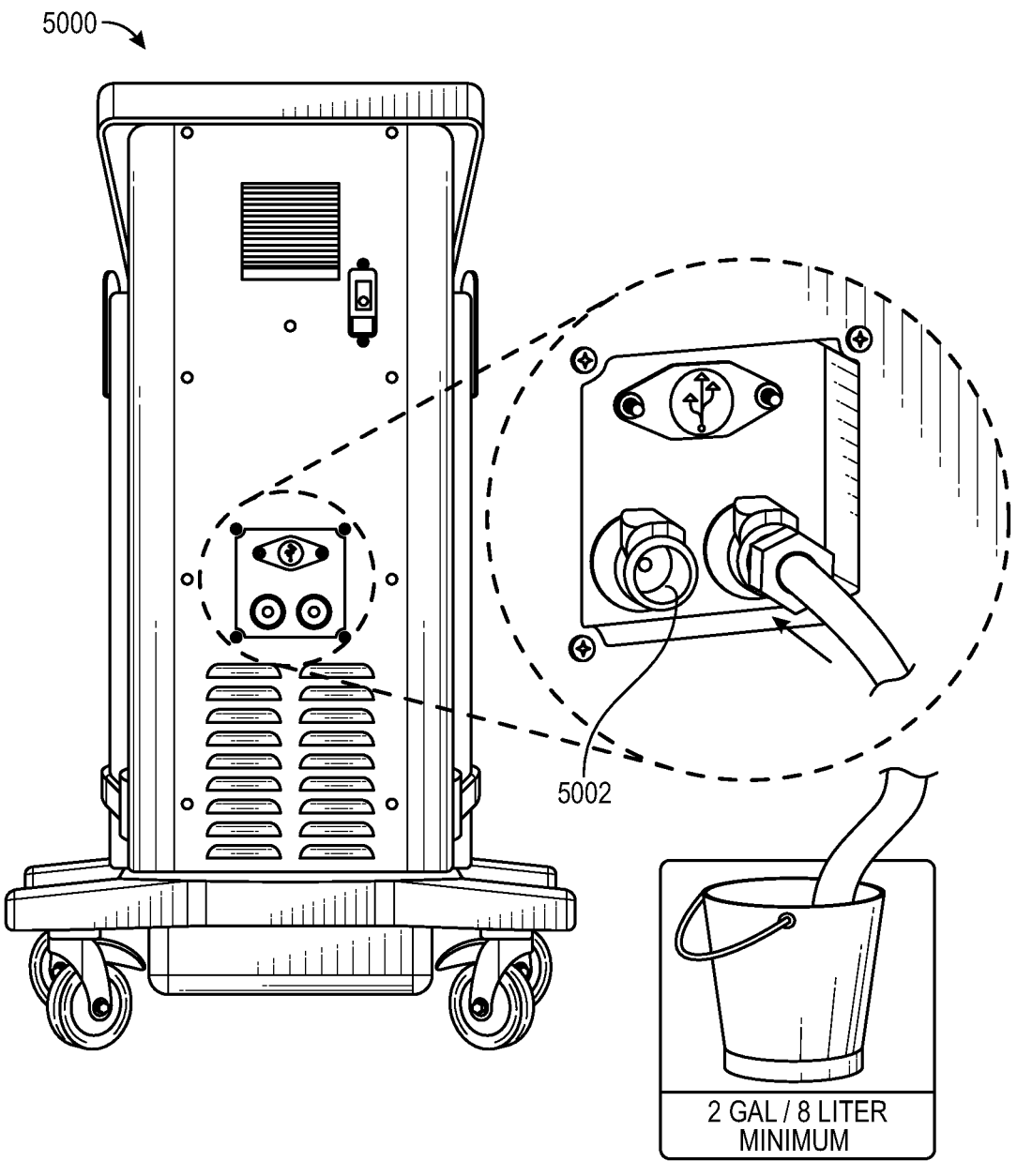

In some embodiments, the system is drained when not in use and drained/refilled periodically. As shown in FIGS. 5A-5C, to facilitate draining and refilling, the system 5000 can have easily accessible drain ports 5002 and fill ports 5004. The fill ports 5004 can be located on the front facing portion of system near the user interface for increased access, which allows the user to easily add more fluid to the system if needed, even during treatment. A removable or openable cover 5006 can cover the fill ports 5004.

Temperature Control:

To make a reasonably sized system, the ratio of thermal mass to heat transfer suggests deviating from the traditional refrigeration temperature control methods.

Figure 6:
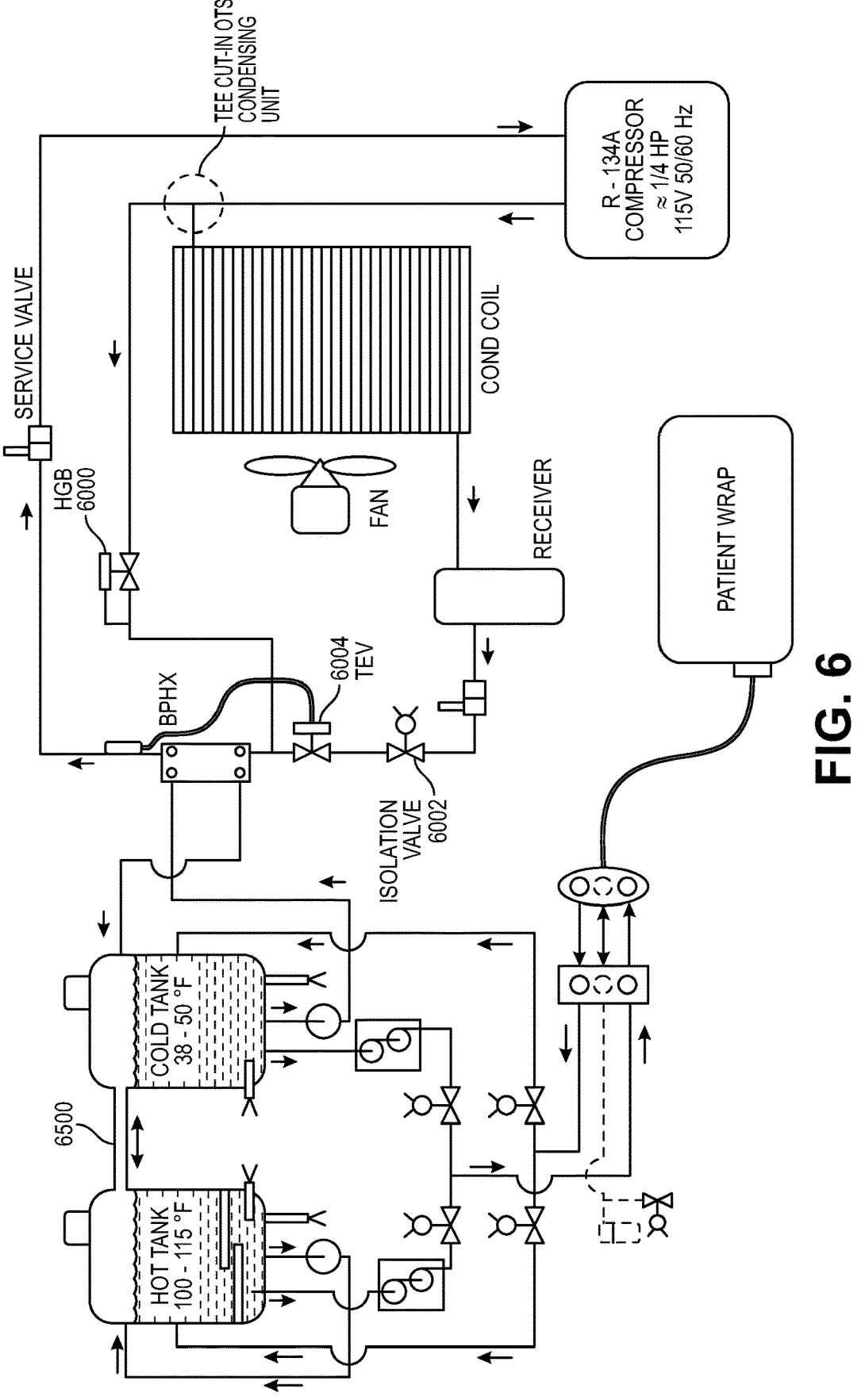
FIGS. 6, 7, 8A and 8B are schematic diagrams that illustrate various embodiments of the system.
Figure 7:
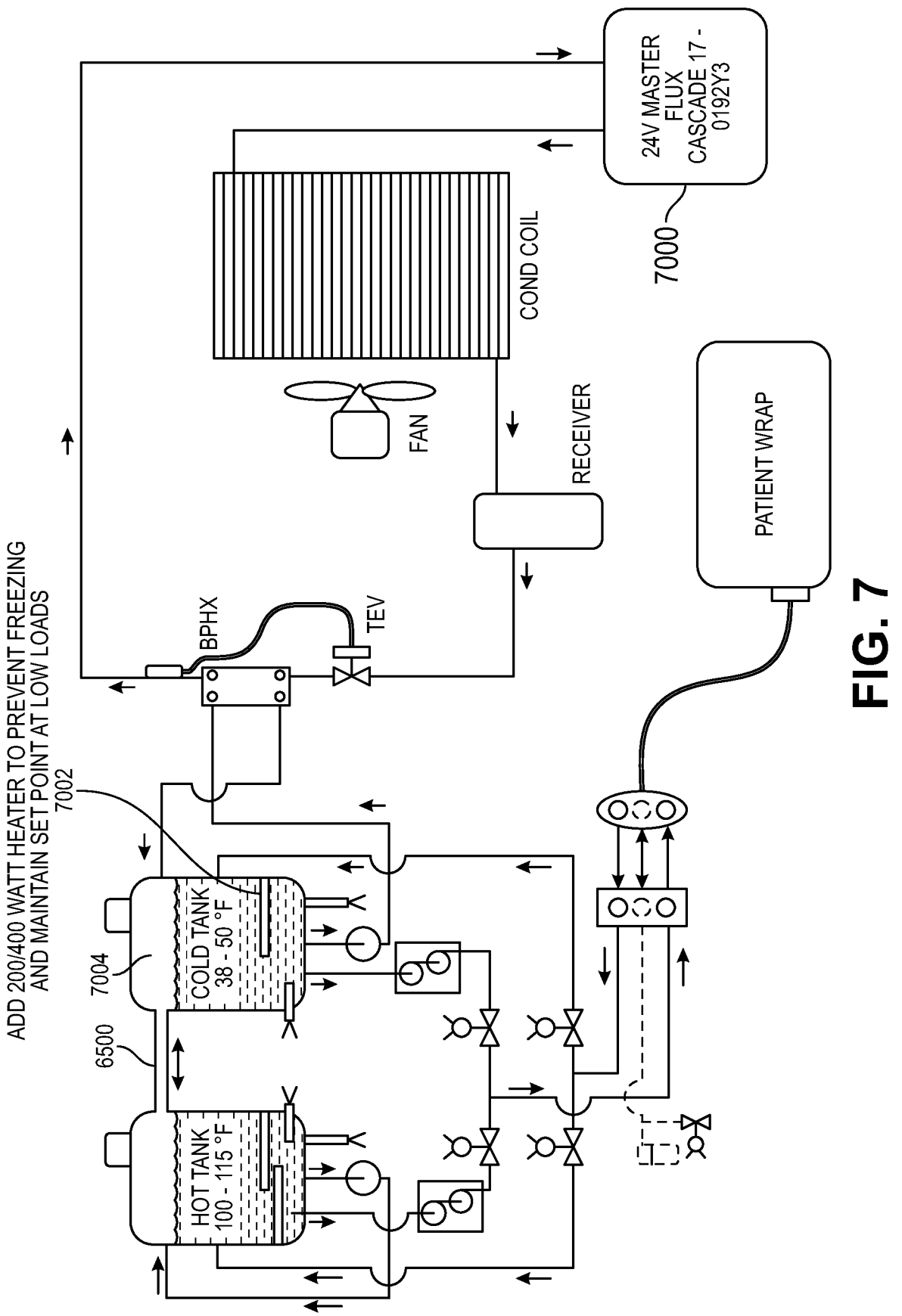
Figure 8A:
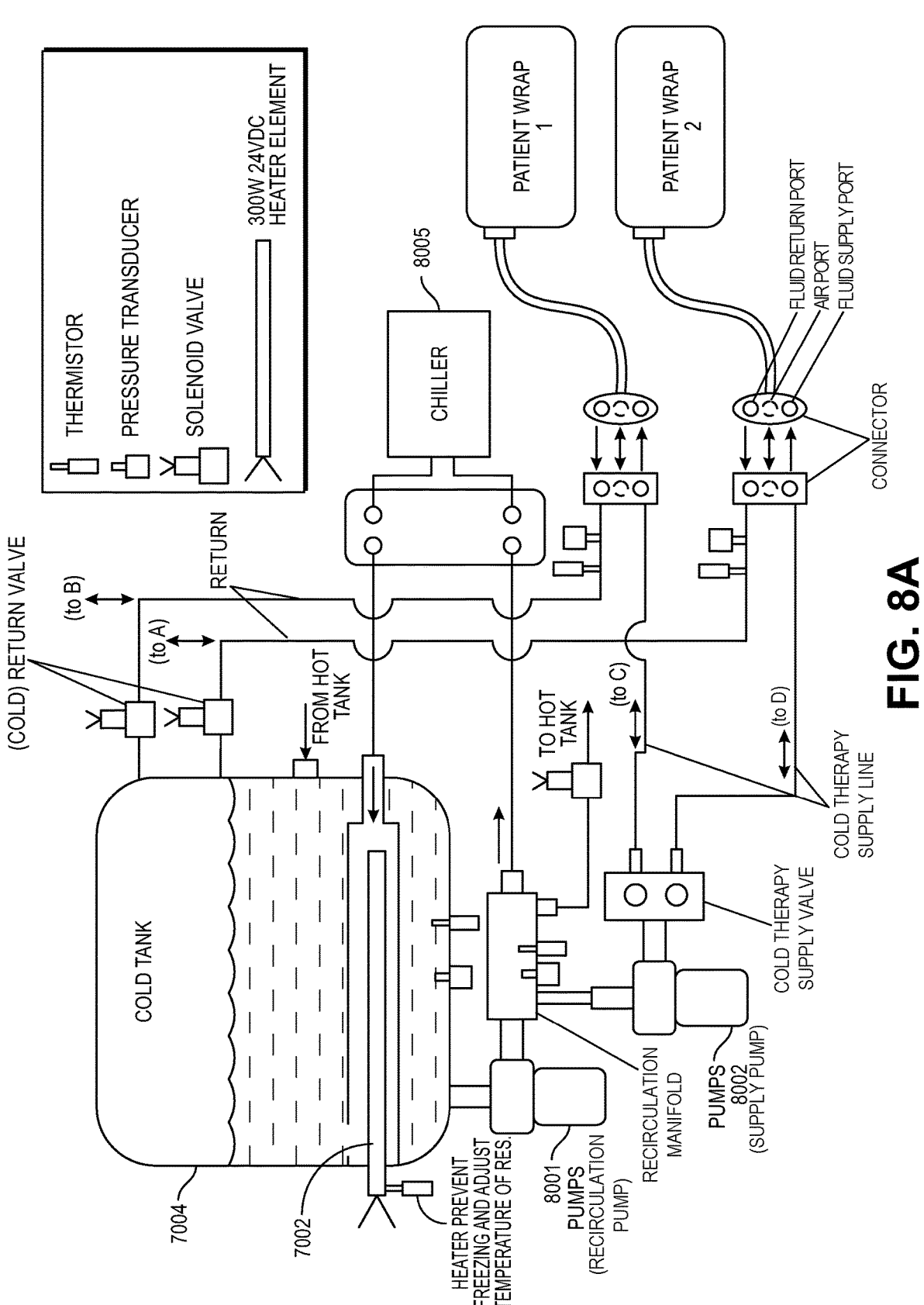
Figure 8B:
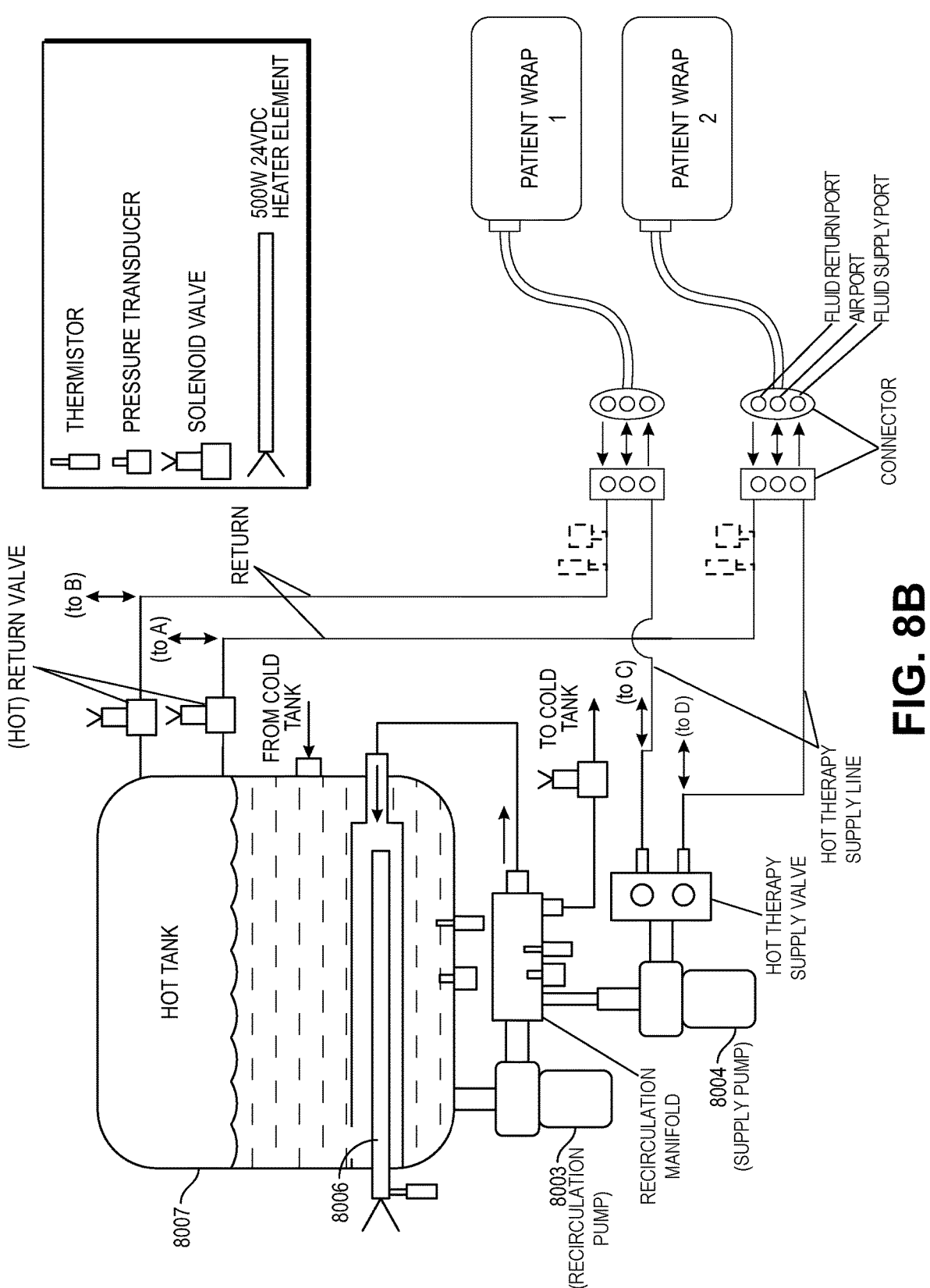

FIGS. 6-8B are schematic diagrams that illustrate various embodiments of the system. As shown in FIG. 6, in some embodiments with an AC system, a hot gas bypass 6000 can be used and temperature can be controlled with an isolation valve 6002 upstream of the thermal expansion valve 6004. As shown in FIG. 7, if a variable speed DC compressor 7000 is used the power may be lowered to allow use of a heater 7002 in the cold tank 7004. FIG. 8A illustrates a schematic of the cold tank portion, and FIG. 8B illustrates a schematic of the hot tank portion. FIGS. 8A and 8B illustrate pumps 8001, 8002, 8003, 8004 that can be used to pump fluid too the chiller 8005, the heater 8006, and between the cold tank 7004 and the hot tank 8007. For example, recirculation pump 8001 can be used to direct flow from the cold tank 7004 to the hot tank 8007, and recirculation pump 8003 can be used to direct flow from the hot tank 8007 to the cold tank 7004. The pumps in combination with a system of valves can be used to control the fluid flow in the system.

Return Water Strategy (i.e. when in Rapid Contrast Mode).

In order to make the cooling and heating systems more efficient, it will be advantageous to delay switching of return water for a period of time after switching from hot to cold or from cold to hot, i.e., when switching from hot to cold, there will be about 300-750 ml or some other volume of hot water still in the hoses and wraps. If return water switched at the same time as the supply water, a large volume of hot water would be pumped into the cold water tank. The inverse would be true when switching from cold back to hot. Return water switching could be delayed until the return water reached a predetermined temperature or time, which can be measured using a temperature sensor, such as a thermistor. Switching between reservoirs can be achieved using solenoid valves that can be opened and closed based on measurements from the temperature sensor. For example:

$$T=(Th-Tc)/2$$

$$T=Th-10 \text{ F (when switching from cold to hot)}$$

$$T=Tc+10 \text{ F (when switching from hot to cold)}$$

$$\text{Time}=60 \text{ seconds}$$

Tank System

When water supply is switched during contrast therapy, the tanks will often be at different levels. There should be a method of protecting the system from overflow of one tank or another, and also a system to prevent one tank from running low on fluid.

A small equalization tube 6500 may be a solution as shown in FIGS. 6 and 7. This equalization tube 6500 would allow the tanks to equalize. The length and diameter of the tube could be sized to prevent fast equalization (which would dump hot water into the cold tank or vice versa). For example, the length and diameter of the tube can be sized to allow up to about 1%, 5%, or 10% of the tank volume in fluid to pass through per minute. The equalization tube 6500 can be located on the upper portion of each tank, such as the upper ½0, ⅒, ⅕, ¼, or ⅓.

A reversible pump between the reservoirs is another possible solution. This would have the advantage of being able to stop or start equalization at any time, and in any direction. Further advantage would be that hot water could be added to the cold tank, or vice versa, in order to more rapidly reach a desired tank temperature (i.e., when changing tank temperatures) or to prevent overshoot, etc.

Another solution can be for overflow to be passed back and forth between the tanks at the filling ports shown in FIG. 5C. The filling ports can be housed in a receptacle that can accommodate fluid overflow from the reservoirs. As one reservoir overflows through its filling port, the receptacle is filled and the overflow fluid flows into the filling port of the other reservoir.

If the liquid levels in the tanks are equilibrated or balanced during therapy, either hot water is added to the cold tank or cold water is added to the hot tank, which reduces the temperature gradient between the hot and cold tanks. This change in tank temperatures during therapy may not be desirable. Therefore, in some embodiments, tank fluid level management, particularly the liquid leveling steps as described herein, can be generally performed outside of therapy, such as after therapy is completed. However, when the liquid level in a tank is critically low, a liquid leveling procedure can be used even during therapy to return the tank levels to non-critical levels. This liquid leveling procedure can be implemented, for example, through control of the pumps described herein in connection with FIGS. 8A and 8B, for example.

It would be advantageous to make filling the system easy and intuitive. Since there will be two tanks, it may be advantageous to only have one fill port, and not have to fill each reservoir individually. In other embodiments, each reservoir can have its own fill port, as shown in FIG. 5B. Directing the water into both the hot tank and cold tank equally may be a challenge. If the fill line is above the level of each reservoir, then both reservoirs would equalize at that point. However, that does not leave room for additional head height in either tank during use, and the two tanks would mix freely, thus making temperature control of each tank more difficult and inefficient. In some embodiments, an indicator on the user interface can indicate the fill level of the reservoirs and/or can indicate when a reservoir is fully filled. The tanks can have a fluid level sensor to determine the amount of fluid in the tank.

Figure 9A:
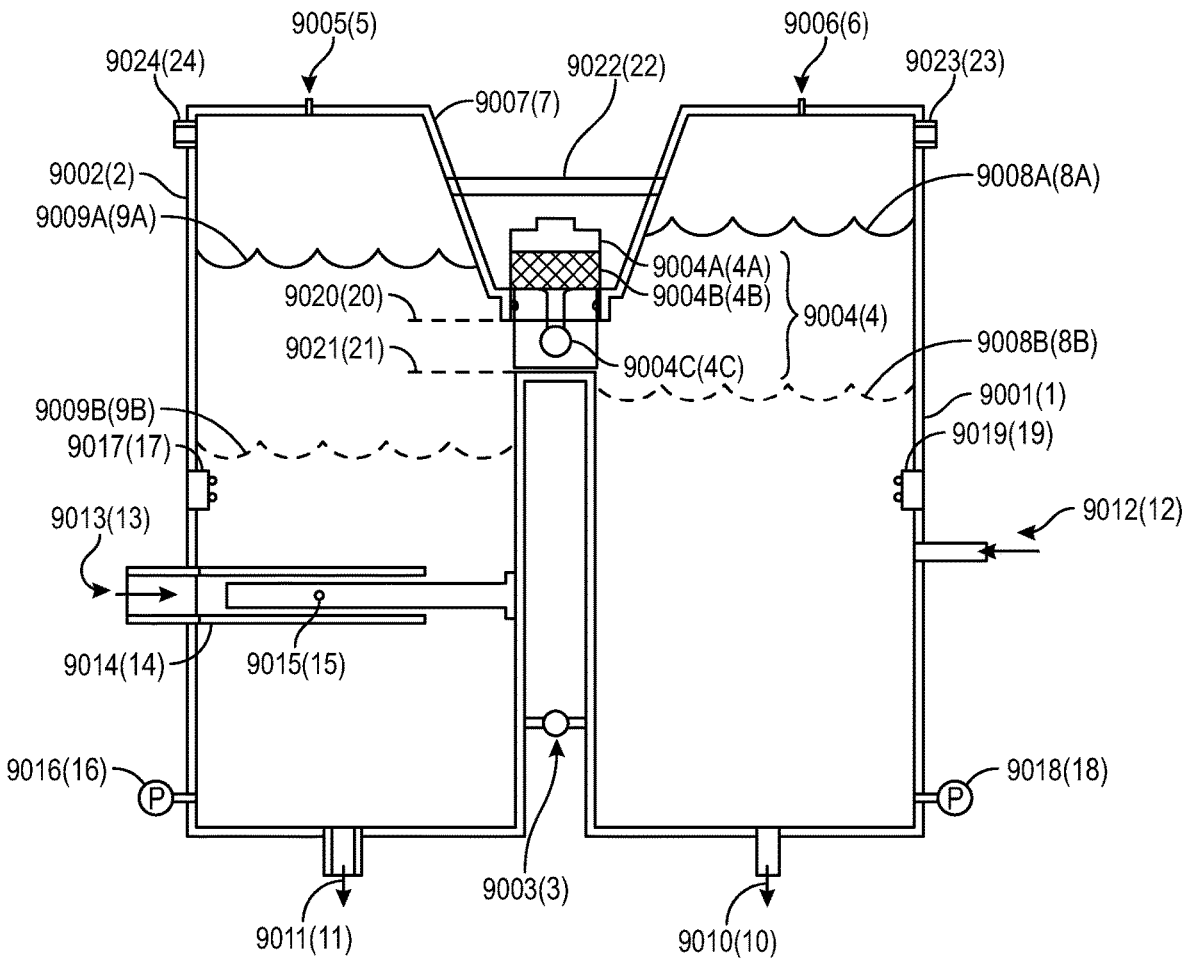

Therefore, an embodiment of a reservoir that addresses these concerns is shown in FIGS. 9A and 9B. The system comprises a Cold Reservoir 9001, a Hot Reservoir 9002 and a Fill Port 9006. Water may be poured into the Fill Port 9007 using a pitcher, hose, gallon jug, etc. Ease of filling may be aided by use of a wide, funnel or tapered shape to the fill port 9007. The fill port 9007 may be sealed by a Fill Cap assembly 9004. The fill cap assembly 9004 may include a Knob 9004A a strainer 9004B and a Tank Seal 9004C. The Tank Seal 9004C may be configured to provide an opening between the reservoirs and the ambient environment in one position (open position), and to seal the opening between the reservoirs and the ambient environment in another position (closed position). In the open position, there may be a conduit that connects the Hot and Cold Reservoirs. This allows for water to equalize between the hot and cold reservoirs once an adequate fill level is attained (between the Upper Fill Level 9020 and Lower Fill Level 9021. When the Tank Seal 9004C is in the Closed Position, the conduit between the Hot and Cold reservoirs may be closed off, in order to prevent exchange of fluid as fluid levels 9008A-B and 9009A-B change independently within the system. Vents 9005, 9006 in the Reservoirs 9002, 9001 allow for the air pressure within the tanks to be nearly atmospheric.

Cold Water Outlet 9010 and Hot Water Outlet 9011 may be located at the bottom surface of the reservoir, or may be at a level just above the reservoir bottom to prevent sediment from entering the fluidics lines. Cold Water Inlet 9012 and Hot Water Inlet 9013 would desirably be configured such to encourage mixing within the reservoir. Proper mixing, or forced convection around the Heater 9015, is particularly important to efficiently heat the water tank, and reduce surface temperature on the heater, which in turn reduces the likelihood of scaling developing on the Heater 9015. For this reason, it may be desirable to include a Heater Baffle 9014 near the heater increase water velocity around the heater surface. The Heater Baffle 9014 may be designed such to provide a torturous water path to further reduce the boundary layer at the surface of the heater. A similar approach may be used if a Heater is used in the Cold Reservoir as well.

A sensor (preferably a Pressure Sensor) may be used in order to sense the water level in the tank. The Pressure Sensor 9016, 9018 would be best placed near the bottom of the tank to most accurately measure Head Pressure within the tank. Reservoir Vents 9005, 9006 would allow for accurate pressure measurement.

Water level may be equalized or adjusted via a Tank Level Facilitator 9003 located adjacent to the reservoirs. The Tank Level Facilitator 9003 may be passive, and could comprise of a simple orifice, or long length of tubing sized to provide a desired flowrate between the two reservoirs base simply on water level difference. The Tank Level Facilitator 9003 may also be an active device that pumps fluid from the Hot Reservoir 9002 to the Cold Reservoir 9001 or vice versa. This may be desirable if a significant water level imbalance is sensed, or to adjust the temperature in one of the tanks rapidly. In addition to or in lieu of the tank head Pressure Sensors 9016, 9018, alternative liquid level sensors or switches may be employed in order to provide a means of identifying whether the tank is above or below a certain point. This may be valuable as a redundant indicator, or to ensure that water was always above the heater element.

An overflow prevention means may be to add an Overflow Conduit 9022 between the two Reservoirs. This may provide for a more rapid exchange of excess water to the opposite tank than could be done with a passive version of the Tank Level Facilitator 9003.

Furthermore, Overflow Drains 9023, 9024 may be utilized in order to route excess water to outside the device, (in an overflow tank, or onto the ground). Additional sensors could be added to the Overflow Drains 9023, 9024 to sense this condition, or a means to detect moisture in the overflow tank could be added.

Parameters for using the system are shown in FIG. 10A-10B.

Figure 11A:
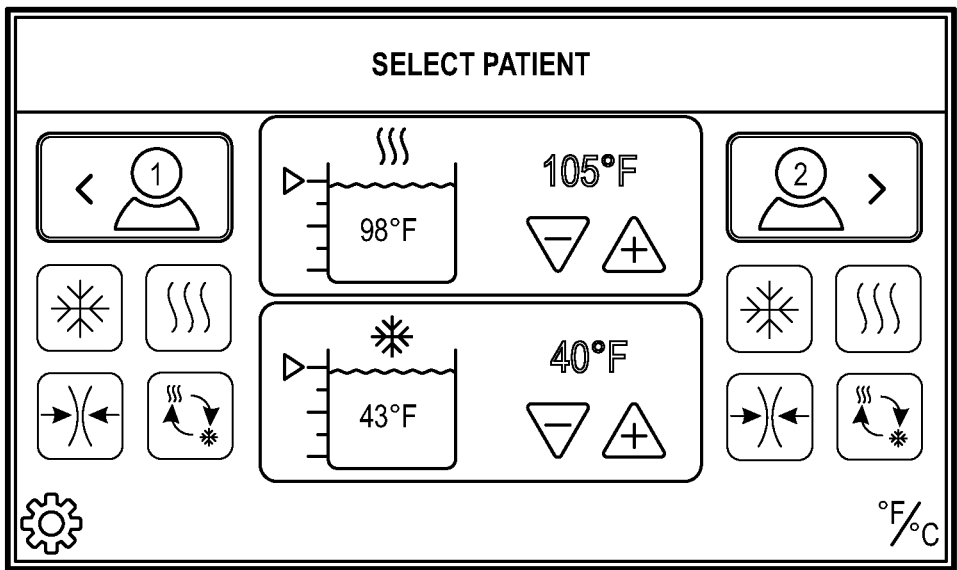
FIGS. 11A-11O illustrate various screens displayed by the touch screen interface.
Figure 11B:
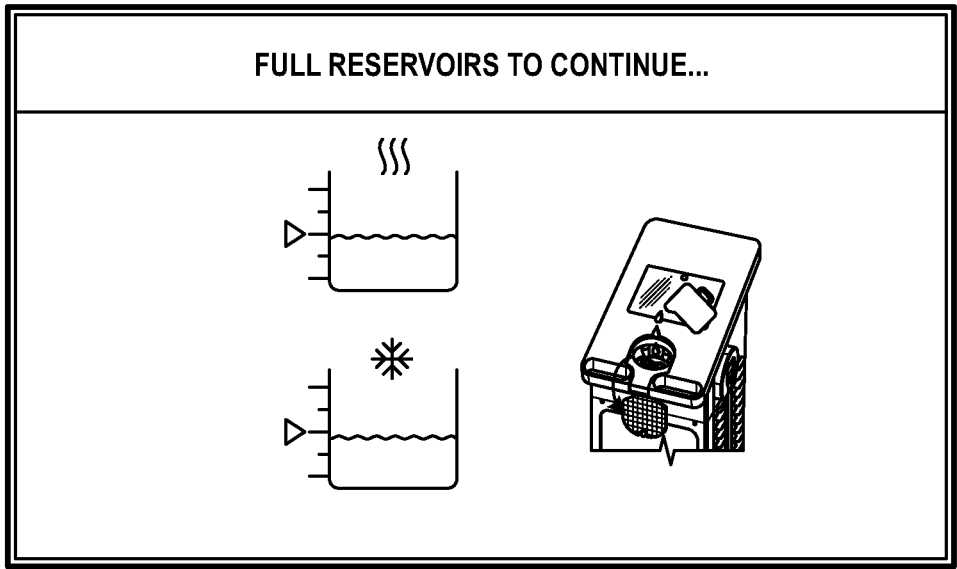
Figure 11C:
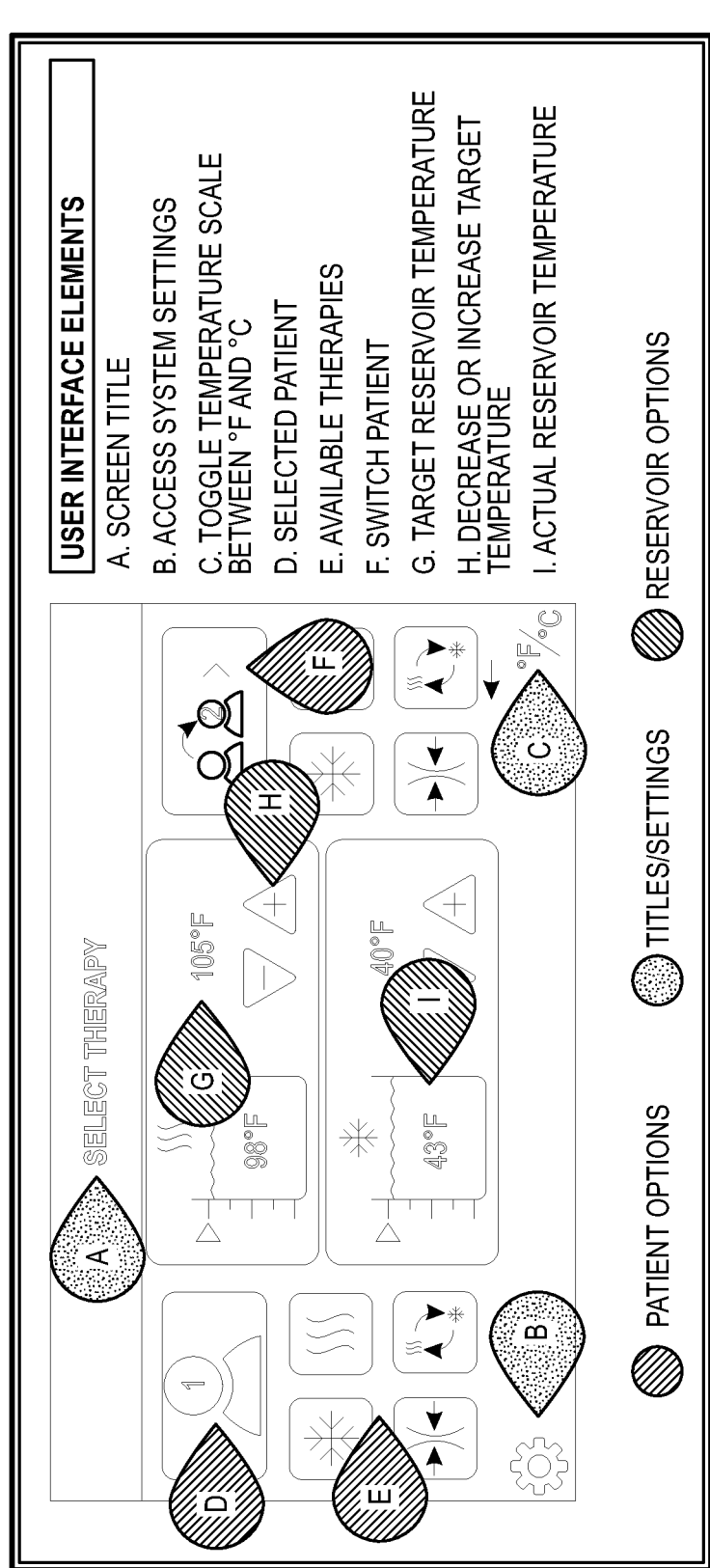
Figure 11D:
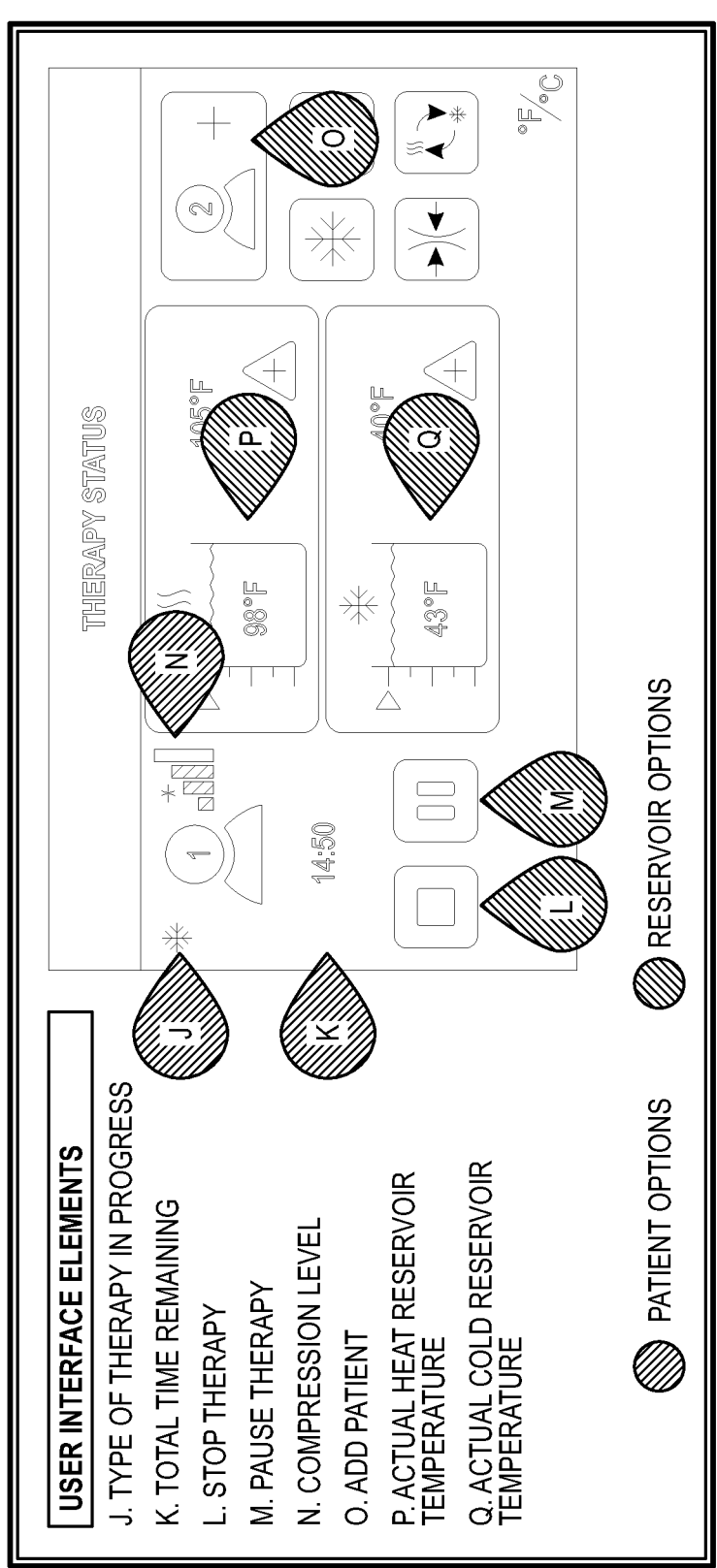
Figure 11G:
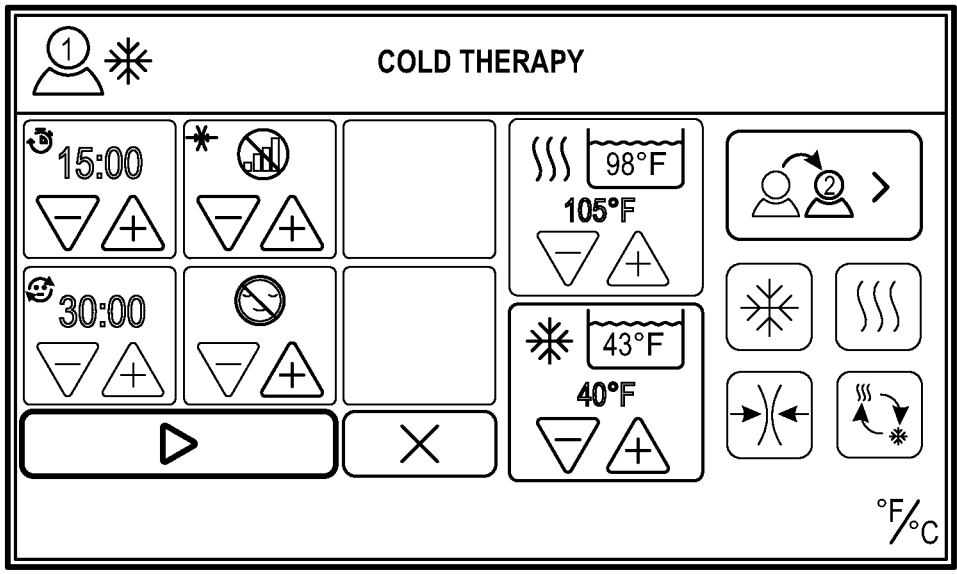
Figure 11H:
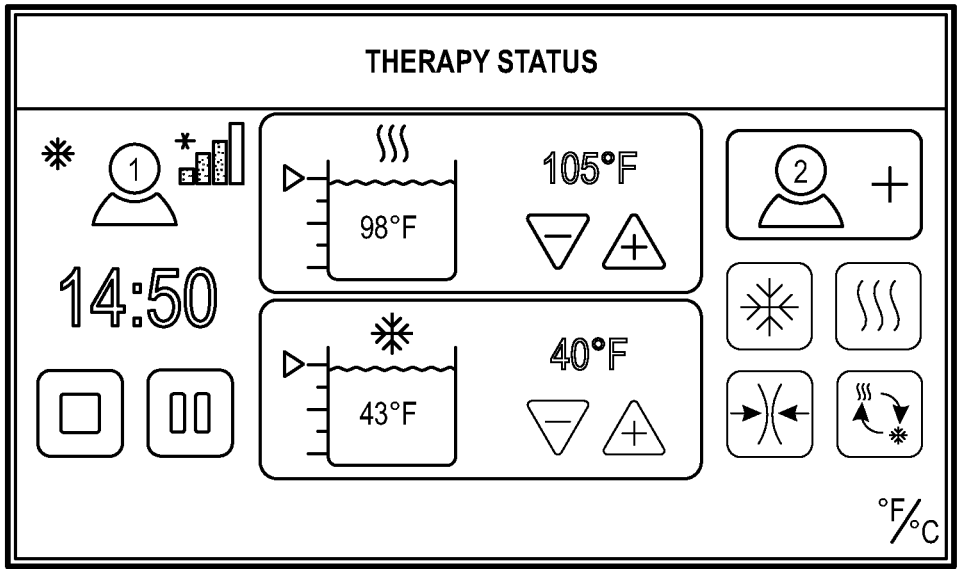
Figure 11I:
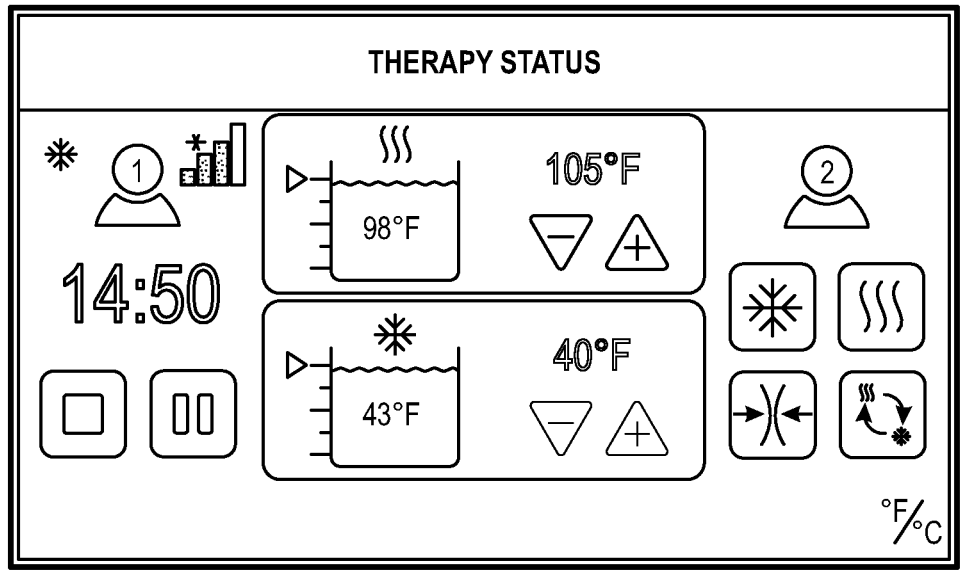
Figure 11J:
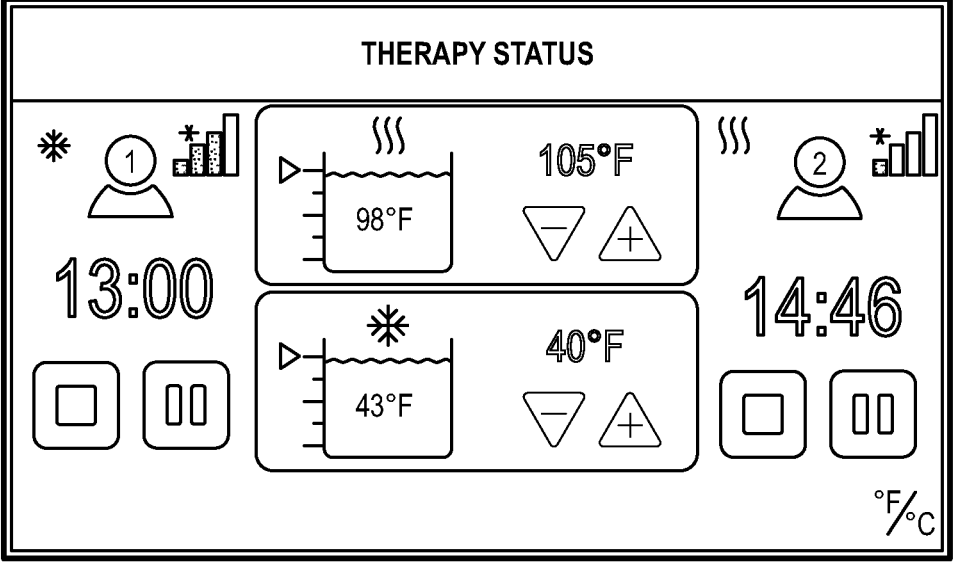
Figure 11K:
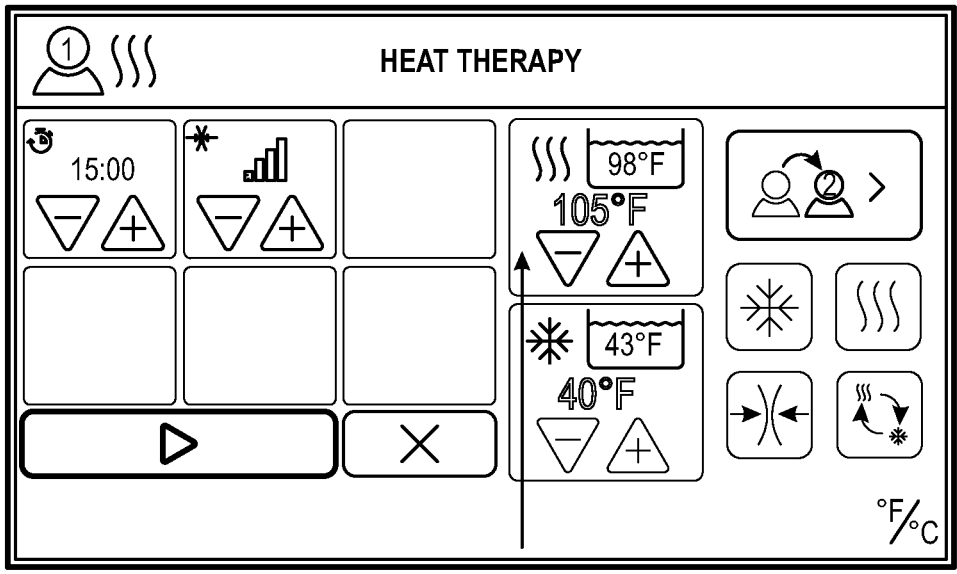
Figure 11L:
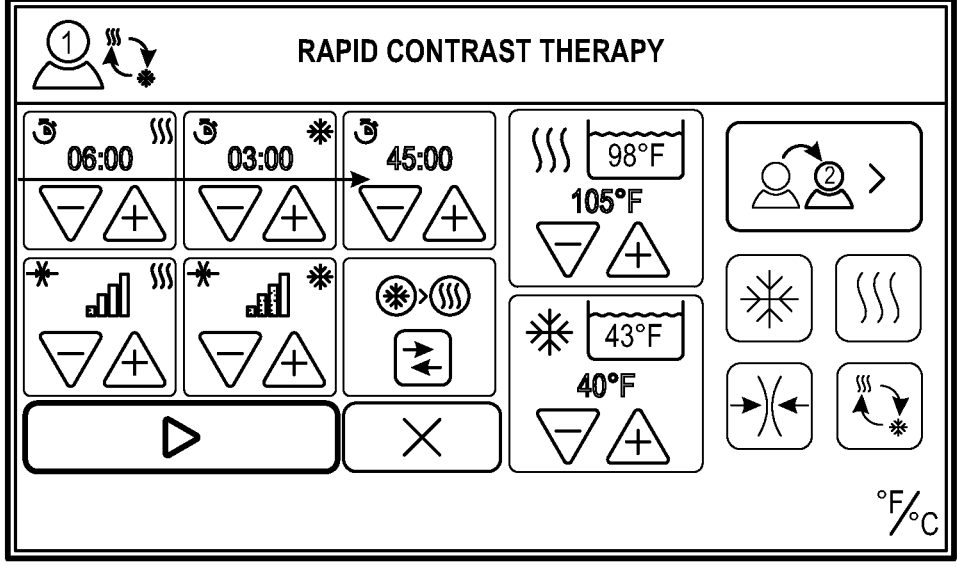
Figure 11M:
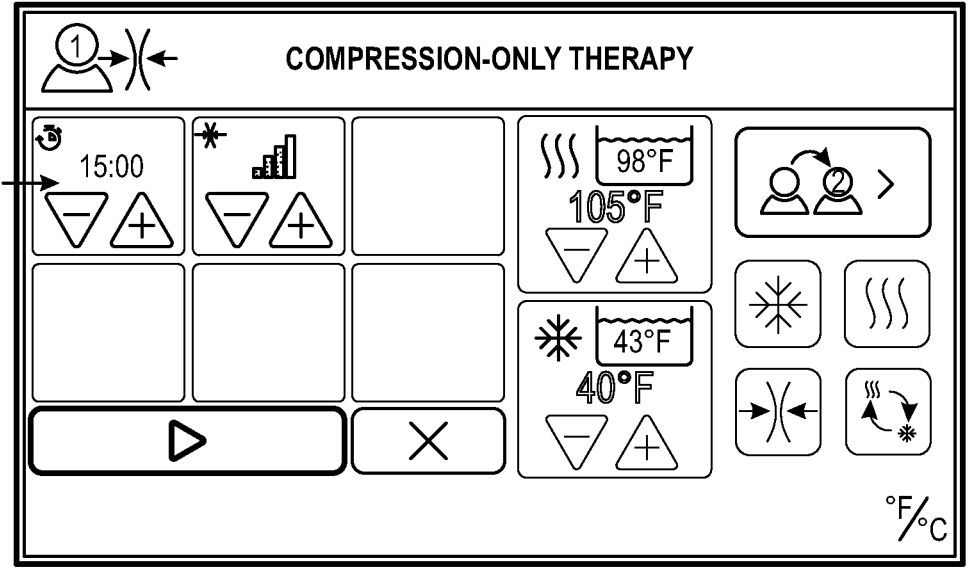
Figure 11N:
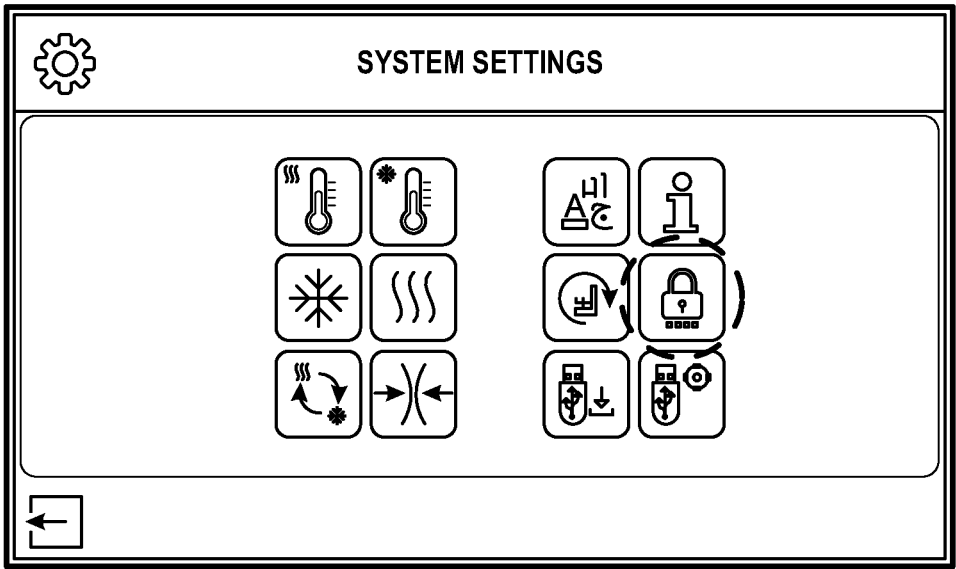
Figure 11O:
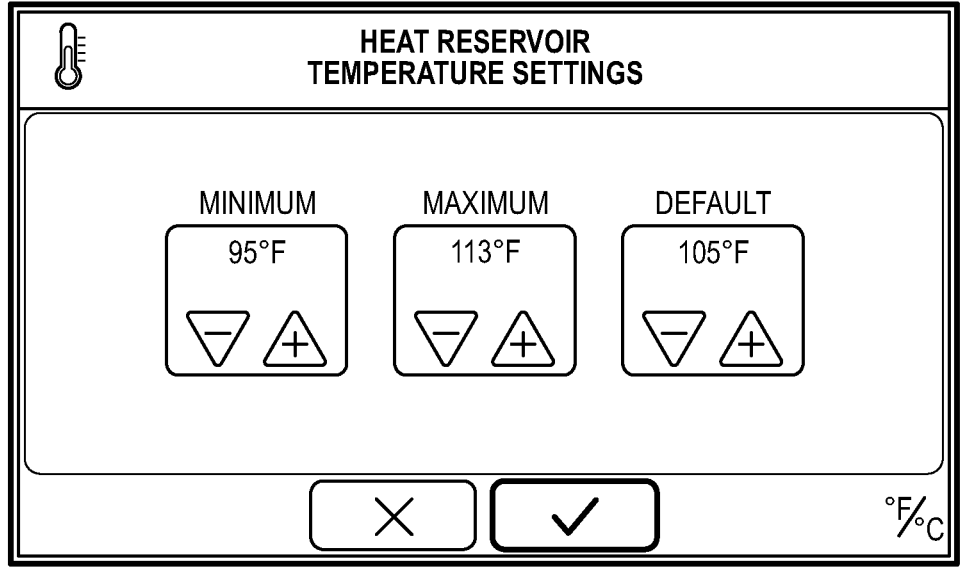

Various screens displayed by the touch screen interface are shown in FIGS. 11A-11O. The system can include a controller and/or processor and memory for storing instructions and programming to implement the user interfaces described herein as well as controlling the system as described herein. The various components, such as the pumps, the sensors, the compressors, the heat exchangers, the heaters, and the valves, can be controlled by the processor and/or send information to the processor.

Thermal Performance Optimization in a Thermal Therapy Device

Hot and Cold Tank reservoir temperatures may deviate if tank level during therapy, as water fills the heat exchangers and then returns to either the hot tank or cold tank. Particularly during contrast therapy, water is returning to either the hot tank or cold tank. In the current embodiment, water is returned to the tank in which the temperature is closest to avoid unnecessary thermal pollution of excessively hot water entering the cold tank, or excessively cold water from entering the hot tank.

Over extended therapy times, or with larger heat exchanger volumes, this may lead to a condition where one of the tanks fills up and the other one gets too empty. This problem may be solved by keeping the tanks equalized during therapy by, for instance, pumping water from the higher tank to the lower tank. Or, connecting the tanks with a small diameter tube to allow tanks to equalize over time. This has the disadvantage of brining the emptier tank away from its set temperature, due to the other tank water entering the tank. For instance, if hot water is pumped into the cold tank to increase the tank level, the hot water will increase the temperature in the cold tank. It is not desirable to have therapy temperatures vary excessively away from the set point in this manner.

Increasing the tank size helps eliminate this condition because if the tank is sufficiently large, there is no worry of getting too full or too empty. However, the larger the tank volume, the longer it takes for reservoir temperatures to reach set point. So excessively large tanks may provide more stable temperature over time and provide plenty of room for large heat exchangers to be used without the tanks getting too full or too empty, but it may take an unacceptable amount of time for the system to reach desired set point. For instance, with 8 liter tanks, when turning the system on in the morning with the reservoir water at room temperature, it may take 30 minutes to reach set point. When with 4 liter tanks, it may only take 15 minutes to reach set point which is more desirable for the customer.

To keep the tanks closest to set point, an algorithm has been developed to optimize water temperature during therapy while keeping tank volumes small enough to allow for acceptable cool down and heat up times.

During therapy, the tanks will not be equalized in order to prevent unnecessary cross tank thermal pollution. However, if the water levels get too low or too full (overflow), preventative steps may be taken: for instance, at a predetermined level, the water returning from the heat exchanger(s) may be diverted to the lower tank instead of the tank of the closest temperature. This is more beneficial than sending water from the opposite tank, as the return water will be closer to the lower tank temperature than the opposite tank. As a further preventative measure, if the tank level gets critically low, cross tank flow may be initiated.

Similarly, if one tank gets too full, it will begin overflowing into the other tank. This causes thermal pollution in a similar manner as cross tank flow.

For instance, the water return valves may perform in the following manner:

If both tank levels exceed 3.75" H2O AND return temperature is greater than average of hot tank recirculating temp and cold tank recirculating temp by more than 0.5° F. then the Hot Tank Return Valve shall be open, otherwise it is closed.

Open Hot Tank Return valve if the hot tank level is ≤3.75" H2O

If hot tank level exceeds 10" H2O, close hot tank valve until hot tank level drops below 7" H2O.

If the Hot tank return valve is closed, then the Cold Tank Return valve shall be open—otherwise it is closed.

And the tank to tank valves may perform in the following manner:

Cold tank to hot tank valve:

By default the valve between the cold tank to hot tank shall be closed.

The valve between the cold tank to hot tank shall perform differently depending on whether Thermal Therapy is active:

When Thermal Therapy is not active or has not been active for 10 seconds, The valve between the cold tank to hot tank shall be open for 5 seconds and then closed for 5 seconds if the cold tank water level is an absolute delta of ¼" (±⅛") greater than the hot tank water level in order to maintain equal tank levels in between therapies.

When Thermal Therapy is active, the valve between the cold tank to hot tank shall be open for 5 seconds and then closed for 5 seconds if the hot tank level is less than 3.6" H2O AND cold tank level exceeds 3.6" H2O.

Hot tank to Cold tank valve

By default the valve between the hot tank to the cold tank shall be closed.

The valve between the hot tank to cold tank shall perform differently depending on whether Thermal Therapy is active:

When Thermal Therapy is not active or has not been active for 10 seconds, The valve between the hot tank to cold tank shall be open for 5 seconds and then closed for 5 seconds if the cold tank water level is an absolute delta of ¼" (±⅛") greater than the hot tank water level in order to maintain equal tank levels in between therapies.

When Thermal Therapy is active, the valve between the hot tank to cold tank shall be open for 5 seconds and then closed for 5 seconds if the hot tank level is less than 3.6" H2O AND cold tank level exceeds 3.6" H2O.

Once therapies end, there will be a tank equalization period where tanks will equalize, at which point the tank with the lower level will get water added from the tank of the higher level. This will thermally pollute one of the tanks, and some time would be required for the tank to get back to set point.

Adding a delay mechanism between the end of therapy and the tank equalization period may be desired in case the user wants to use the system right away while the tanks are near their set temperature. The delay could be a fixed period of time (i.e. 10 seconds), or could take the form of a "do not equalize" button.

Figure 12:
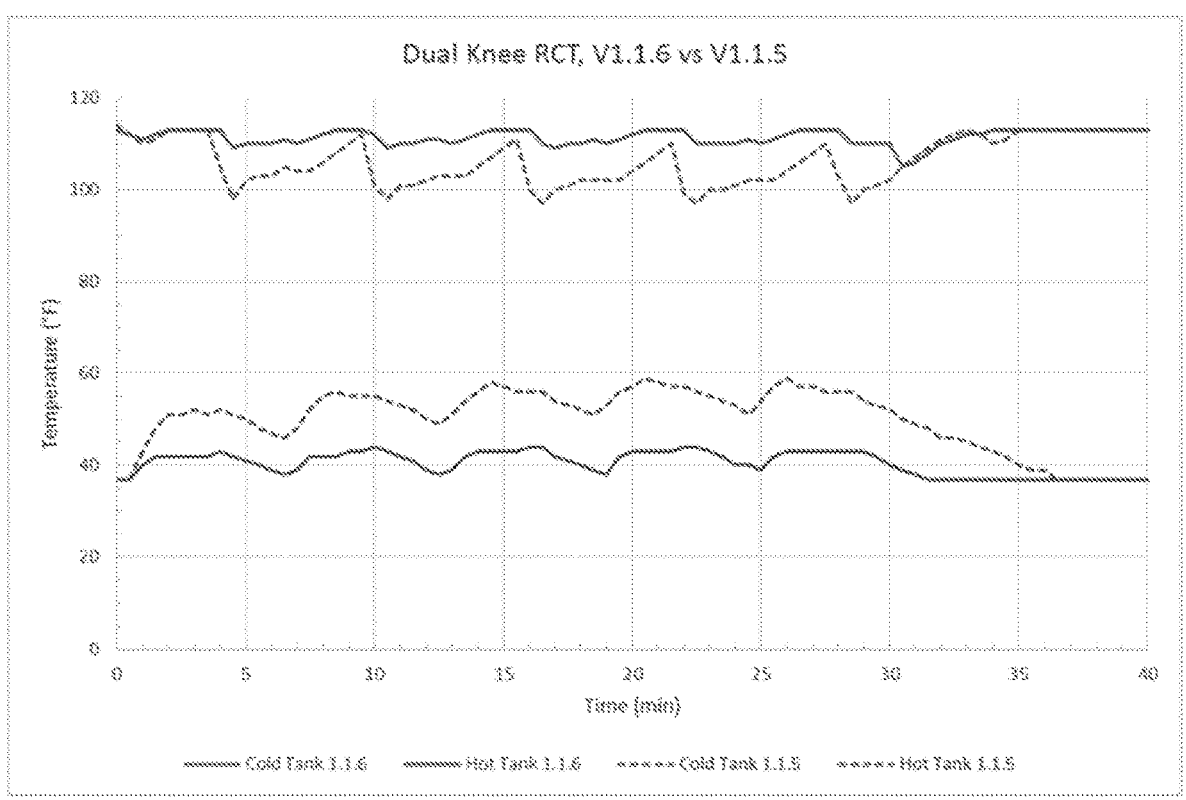
FIG. 12 is graph of tank temperatures using various temperature control algorithms.

A graph of the thermal performance is shown in FIG. 12 and is presented as an example of tank temperatures before and after the enhanced algorithm. The therapy in the example below is a Rapid Contrast Therapy with a straight knee wrap on each port (port 1 and port 2) with 3 minutes on cold, followed by 3 minutes on hot therapy, alternating back and forth for a total of 30 minutes. Two versions of software (containing the algorithms) are presented. V1.1.6 is the improved algorithm that does not equalize the tanks during therapy. V1.1.5 keeps tanks equalized during therapy to within a certain limit.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present.

In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the disclosure. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present disclosure.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the disclosure as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the disclosure as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "disclosure" merely for convenience and without intending to voluntarily limit the scope of this application to any single disclosure or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:
1. A system for providing rapid contrast therapy, the system comprising:

a cold reservoir configured to hold a cold liquid, the cold reservoir including a first liquid level sensor to measure a level of the cold liquid and a first temperature sensor to measure a temperature of the cold liquid;

a hot reservoir configured to hold a hot liquid, the hot reservoir including a second liquid level sensor to measure a level of the hot liquid and a second temperature sensor to measure a temperature of the hot liquid;

a return valve for directing return flow from a therapy device to the hot reservoir and the cold reservoir;

a return temperature sensor for measuring a temperature of the return flow from the therapy device; and a controller directing operation of the return valve to control the return flow from the therapy device to the cold and hot reservoirs, wherein the controller is configured to:

responsive to determining that the level of the cold liquid and the hot liquid are within a target liquid level range, direct the return flow to one of the cold reservoir or the hot reservoir having a closest temperature with the temperature of the return flow, and responsive to determining that the level of either the cold liquid or the hot liquid falls below a lower limit of the target liquid level range, direct the return flow to a corresponding one of the cold reservoir or the hot reservoir.

2. The system of claim 1, wherein the controller is further configured to:

responsive to determining that the level of either the cold liquid or the hot liquid exceeds an upper limit of the target liquid level range, direct the return flow to an opposite one of the cold reservoir or the hot reservoir.

3. The system of claim 1, further comprising:

a cold therapy supply valve in fluid communication with the cold reservoir, the cold therapy supply valve directing a flow of the cold liquid to a therapy device; and a hot therapy supply valve in fluid communication with the hot reservoir, the hot therapy supply valve directing a flow of the hot liquid to the therapy device, wherein the controller directs operation of the cold therapy supply valve and the hot therapy supply valve.

4. The system of claim 1, further comprising:

a conduit extending between the cold reservoir and the hot reservoir, the conduit providing fluid communication therebetween; and one or more cross-tank valves for controlling flow through the conduit, wherein:

the controller directs operation of the one or more cross-tank valves to control flow between the cold and hot reservoirs, and the controller directs operation of the one or more cross-tank valves in response to a measured liquid level in each of the cold and hot reservoirs such that the level of the cold liquid in the cold reservoir and the level of the hold liquid in the hot reservoir do not exceed an upper limit or fall below the lower limit of the target liquid level range.

5. The system of claim 4, wherein the controller directs flow through the conduit:

from the hot reservoir to the cold reservoir when the first liquid level sensor measures a liquid level below the lower limit of the target liquid level range, from the cold reservoir to the hot reservoir when the second liquid level sensor measures a liquid level below the lower limit of the target liquid level range, from the cold reservoir to the hot reservoir when the first liquid level sensor measures a liquid level above the upper limit of the target liquid level range, or from the hot reservoir to the cold reservoir when the second liquid level sensor measures a liquid level above upper limit of the target liquid level range.

6. The system of claim 4, wherein the system is not operating when at least one of the cold and hot liquids have not been provided to the therapy device for a predetermined off period and, when the system is not operating, the controller directs operation of one or more of the cross-tank valves to open fluid communication between the cold and hot reservoirs for a first time period.

7. The system of claim 6, wherein the predetermined off period that the system is not operating is between 5 and 20 seconds.

8. The system of claim 6, wherein the controller directs operation of one or more of the cross-tank valves to open fluid communication between the reservoirs until a difference between the measured liquid levels in the cold and hot reservoirs is within a predetermined deviation amount.

9. The system of claim 6, wherein the controller directs cycled operation of one or more of the cross-tank valves to open and close fluid communication between the reservoirs, such that during each open-close cycle the one or more of cross-tank valves is open for the first time period and closed for a second time period until a difference between the measured liquid levels in the cold and hot reservoirs is within a predetermined deviation amount.

10. A method of operating a rapid contrast therapy device, the method comprising:

measuring liquid levels of both a cold liquid within a cold liquid reservoir and a hot liquid within a hot liquid reservoir of the rapid contrast therapy device;

determining whether the measured liquid levels are within a target liquid level range; and controlling, via a return valve, a return flow of liquid from a therapy wrap of the rapid contrast therapy device to at least one of the cold liquid reservoir or the hot liquid reservoir to minimize thermal pollution of hot water from entering the cold liquid reservoir or cold water from entering the hot liquid reservoir upon return from the therapy wrap, wherein:

responsive to determining, by a controller, that the level of the cold liquid and the hot liquid are within a target liquid level range, the return flow is directed to one of the cold liquid reservoir or the hot liquid reservoir having a closest temperature with a temperature of the return flow, and responsive to determining, by the controller, that the level of either the cold liquid or the hot liquid falls below a lower limit of the target liquid level range, the return flow directed to a corresponding one of the cold liquid reservoir or the hot liquid reservoir.

11. The method of claim 10, wherein responsive to determining, by the controller, that the level of either the cold liquid or the hot liquid exceeds an upper limit of the target liquid level range, the return flow is directed to an opposite one of the cold liquid reservoir or the hot liquid reservoir.

12. The method of claim 10, wherein the rapid contrast therapy device includes a conduit extend between the cold liquid reservoir and the hot liquid reservoir and a cross-tank valve for controlling flow through the conduit, the method further comprising:

operating the cross-tank valve to allow fluid to flow between the cold and hot liquid reservoirs such that the liquid level in either the cold and hot liquid reservoirs does not exceed an upper limit or fall below the lower limit of the target liquid level range.

13. The method of claim 12, the method further comprising operating the cross-tank valve to direct flow through the conduit:

from the hot liquid reservoir to the cold liquid reservoir when the level of the cold liquid falls below the lower limit of the target liquid level range, from the cold liquid reservoir to the hot liquid reservoir when the level of the hot liquid falls below the lower limit of the target liquid level range, from the cold liquid reservoir to the hot liquid reservoir when the level of the cold liquid exceeds the upper limit of the target liquid level range, or from the hot liquid reservoir to the cold liquid reservoir when the level of the hot liquid exceeds the upper limit of the target liquid level range.

14. The method of claim 12, wherein the rapid contrast therapy device is not operating when at least one of the cold and hot liquids have not been provided to the therapy wrap for a predetermined off period, wherein, when the rapid contrast therapy device is not operating, the method further includes opening the cross-tank valve for a first time period.

15. The method of claim 14, wherein the predetermined off period that the rapid contrast therapy device is not operating is between 5 and 20 seconds.

16. The method of claim 14, wherein the cross-tank valve is held open until a difference between the measured liquid levels in the cold and hot liquid reservoirs is within a predetermined deviation amount.

17. The method of claim 14, further comprising:

cyclically operating the cross-tank valve to open and close fluid communication between the cold and hot liquid reservoirs, such that during each open-close cycle the cross-tank valve is open for the first time period and closed for a second time period until a difference between the measured liquid levels in the cold and hot liquid reservoirs is within a predetermined deviation amount.

18. A controller for a rapid contrast therapy device, the controller comprising:

a processor; and memory having instructions stored thereon that, when executed by the processor, cause the controller to:

measure liquid levels of both a cold liquid within a cold liquid reservoir and a hot liquid within a hot liquid reservoir of the rapid contrast therapy device;

determine whether the measured liquid levels are within a target liquid level range; and control a return valve of the rapid contrast therapy device to direct a return flow of liquid from a therapy wrap of the rapid contrast therapy device to at least one of the cold liquid reservoir or the hot liquid reservoir, wherein responsive to determining, by a controller, that the level of the cold liquid and the hot liquid are within a target liquid level range, the return flow is directed to one of the cold liquid reservoir or the hot liquid reservoir having a closest temperature with the temperature of the return flow, and responsive to determining, by the controller, that the level of either the cold liquid or the hot liquid falls below a lower limit of the target liquid level range, the return flow is directed to a corresponding one of the cold liquid reservoir or the hot liquid reservoir.

19. The controller of claim 18, wherein if the level of either the cold liquid or the hot liquid exceeds an upper limit of the target liquid level range, the return flow is directed to an opposite one of the cold liquid reservoir or the hot liquid reservoir.

20. The controller of claim 18, wherein the instructions further cause the controller to:

control a cross-tank valve on a conduit extending between the cold liquid reservoir and the hot liquid reservoir of the rapid contrast therapy device to direct flow through the conduit such that the liquid level in either the cold and hot liquid reservoirs does not exceed an upper limit or fall below the lower limit of the target liquid level range.

* * * * *